(12) United States Patent
Hester et al.

(10) Patent No.: US 12,303,493 B2
(45) Date of Patent: May 20, 2025

(54) ANTICANCER COMPOSITIONS

(71) Applicant: Aragon Pharmaceuticals, Inc., Los Angeles, CA (US)

(72) Inventors: Dennis Martin Hester, San Diego, CA (US); Jason Michael Vaughn, High Point, NC (US)

(73) Assignee: Aragon Pharmaceuticals, Inc., Los Angeles, CA (US)

( * ) Notice: Subject to any disclaimer, the term of this patent is extended or adjusted under 35 U.S.C. 154(b) by 0 days.

(21) Appl. No.: 18/660,698

(22) Filed: May 10, 2024

(65) Prior Publication Data

US 2024/0293374 A1 Sep. 5, 2024

Related U.S. Application Data

(63) Continuation of application No. 18/192,244, filed on Mar. 29, 2023, which is a continuation of application
(Continued)

(30) Foreign Application Priority Data

Dec. 5, 2014 (EP) .................................. 141965947

(51) Int. Cl.
*A61K 31/4184* (2006.01)
*A61K 9/00* (2006.01)
(Continued)

(52) U.S. Cl.
CPC ........ *A61K 31/4184* (2013.01); *A61K 9/0053* (2013.01); *A61K 9/141* (2013.01);
(Continued)

(58) Field of Classification Search
CPC . A61K 31/4184; A61K 9/0053; A61K 9/2054
See application file for complete search history.

(56) References Cited

U.S. PATENT DOCUMENTS 9,387,216 B2 7/2016 Njar et al.
9,987,261 B2 6/2018 Jung et al.
(Continued)

FOREIGN PATENT DOCUMENTS

BR 112016002970-4 A2 9/2017
CA 2940984 A1 8/2015
(Continued)

OTHER PUBLICATIONS

"Australian Public Assessment Report for Apalutamide, Proprietary Product Name: Erlyand/Janssen Apalutamide", Mar. 2019, pp. 84.
(Continued)

*Primary Examiner* — San Ming R Hui
(74) *Attorney, Agent, or Firm* — BakerHostetler

(57) ABSTRACT

The present invention concerns pharmaceutical formulations of ARN-509, which can be administered to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. In one aspect, these formulations comprise a solid dispersion of ARN-509 and HPMCAS. In one aspect, the solid dispersion of ARN-509 and HPMCAS is obtainable, in particular is obtained, by melt-extruding a mixture comprising ARN-509 and HPMCAS and optionally subsequently milling said melt-extruded mixture. In one aspect, the solid dispersion of ARN-509 and HPMCAS is obtainable, in particular is obtained, by spray drying a mixture comprising ARN-509 and HPMCAS in a suitable solvent.

30 Claims, 3 Drawing Sheets

Related U.S. Application Data

No. 15/533,188, filed as application No. PCT/US2015/063661 on Dec. 3, 2015, now abandoned.

(51) Int. Cl.
   *A61K 9/14* (2006.01)
   *A61K 9/16* (2006.01)
   *A61K 9/20* (2006.01)

(52) U.S. Cl.
   CPC .............. *A61K 9/16* (2013.01); *A61K 9/1652* (2013.01); *A61K 9/1682* (2013.01); *A61K 9/2054* (2013.01); *A61K 9/2077* (2013.01)

(56) References Cited

U.S. PATENT DOCUMENTS

| | | |
|---|---|---|
| 10,285,948 B2 | 5/2019 | Verreck |
| 11,224,575 B2 | 1/2022 | Verreck |
| 2003/0054038 A1 | 3/2003 | Crew et al. |
| 2003/0068374 A1 | 4/2003 | Kamei et al. |
| 2010/0310659 A1 | 12/2010 | Desai et al. |
| 2011/0003839 A1 | 1/2011 | Jung et al. |
| 2013/0116258 A1 | 5/2013 | Smith et al. |
| 2013/0224301 A1 | 8/2013 | Curatolo et al. |
| 2013/0345320 A1 | 12/2013 | Kolter et al. |
| 2014/0088129 A1 | 3/2014 | Chen |
| 2014/0100256 A1 | 4/2014 | Lorenz et al. |
| 2014/0105933 A1 | 4/2014 | Kumar et al. |
| 2014/0287039 A1 | 9/2014 | Bosch et al. |
| 2015/0037407 A1 | 2/2015 | Bandyopadhyay et al. |
| 2015/0209359 A1 | 7/2015 | Yaffe et al. |
| 2015/0374721 A1 | 12/2015 | Njar et al. |
| 2016/0346207 A1 | 12/2016 | Grahek et al. |
| 2017/0360713 A1 | 12/2017 | Verreck |
| 2017/0360754 A1 | 12/2017 | Hester et al. |
| 2019/0216829 A1 | 7/2019 | Bertels et al. |
| 2020/0163882 A1 | 5/2020 | Grahek et al. |
| 2021/0308060 A1 | 10/2021 | Verreck |
| 2023/0233529 A1 | 7/2023 | Hester et al. |

FOREIGN PATENT DOCUMENTS

| | | |
|---|---|---|
| CN | 1545421 A | 11/2004 |
| CN | 1571658 A | 1/2005 |
| CN | 1787808 A | 6/2006 |
| CN | 101450212 A | 6/2009 |
| CN | 101454002 A | 6/2009 |
| CN | 102525876 A | 7/2012 |
| CN | 102884057 A | 1/2013 |
| CN | 105246598 A | 1/2016 |
| CN | 105636594 A | 6/2016 |
| CN | 106102716 A | 11/2016 |
| CN | 106999431 B | 3/2022 |
| EP | 0901786 A2 | 3/1999 |
| EP | 1368001 A2 | 12/2003 |
| EP | 1399190 A1 | 3/2004 |
| EP | 3812378 A1 | 4/2021 |
| EP | 3226843 B1 | 5/2021 |
| IN | 201637029773 | 11/2016 |
| JP | 11-116502 A | 4/1999 |
| JP | 2004-534822 A | 11/2004 |
| JP | 2009-531439 | 9/2009 |
| JP | 2017-507928 A | 3/2017 |
| JP | 6830892 B2 | 2/2021 |
| KR | 10-2016-0113294 A | 9/2016 |
| KR | 10-2017-0086658 A | 7/2017 |
| MX | 2016010216 A | 11/2016 |
| WO | 93/20097 A1 | 10/1993 |
| WO | 02/67893 A2 | 9/2002 |
| WO | 02/80902 A1 | 10/2002 |
| WO | 03/00292 A1 | 1/2003 |
| WO | 2003/063821 A2 | 8/2003 |
| WO | 03/77827 A1 | 9/2003 |
| WO | 2005/055987 A1 | 6/2005 |
| WO | 2006/085089 A1 | 8/2006 |
| WO | 2007/126765 A3 | 11/2008 |
| WO | 2011/103202 A2 | 8/2011 |
| WO | 2012/174436 A1 | 12/2012 |
| WO | 2013/152342 A1 | 10/2013 |
| WO | 2013/184681 A1 | 12/2013 |
| WO | 2014/031422 A1 | 2/2014 |
| WO | 2014/043208 A1 | 3/2014 |
| WO | 2014/052237 A1 | 4/2014 |
| WO | 2014/113260 A1 | 7/2014 |
| WO | 2014/114575 A1 | 7/2014 |
| WO | 2014/167428 A2 | 10/2014 |
| WO | 2015/023710 A1 | 2/2015 |
| WO | 2015/118015 A1 | 8/2015 |
| WO | 2016/021707 A1 | 2/2016 |
| WO | 2016/090098 A1 | 6/2016 |
| WO | 2016/090101 A1 | 6/2016 |
| WO | 2016/090105 A1 | 6/2016 |

OTHER PUBLICATIONS

Silverman, "The Organic Chemistry of Drug Design and Drug Action ", Second edition, 2004, pp. 4.

Volkova et al., "Effect of polymers and cyclodextrins on solubility, permeability and distribution of enzalutamide and apalutamide antiandrogens", Journal of Molecular Liquids, Nov. 30, 2020, vol. 322, pp. 34.

Wei R., "Spirocyclic Compound", Chemical Industry press, Aug. 2007.

Chavan et al., Cellulose based polymers in development of amorphous solid dispersions, Asian J of Pharm Sci, 14, 2019, 248-264.

Ji et al., Enzalutamide and Apalutamide: In Vitro Chemical Reactivity Studies and Activity in a Mouse Drug Allergy Model, Chem. Res. Toxicol. 2020, 33, 211-222.

Williams et al., Strategies to Address Low Drug Solubility in Discovery and Development, Pharmacol Rev, Jan. 2013, vol. 65, pp. 315-499.

Wilson et al., Relationship between amorphous solid dispersion in vivo absorption and in vitro dissolution: phase behavior during dissolution, speciation, and membrane mass transport, J of Contr Release, 292, 2018, 172-182.

Shin-Etsu AQOAT, "NF Hypromellose Acetate Succinate", 2005, pp. 1-20.

Srikanth et al., "Studies on the Effect of Hydrophilic Carriers in the Dissolution Rate Enhancement of Poorly Soluble Drug, Bicalutamide," Research J. Pharm. And Tech., vol. 3, No. 2, 2010, pp. 592-595.

Srinarong et al., "Improved Dissolution Behavior of Lipophilic Drugs By Solid Dispersions: The Production Process as Starting Point For Formulation Considerations", Expert Opin. Drug Deliv., vol. 8, No. 9, 2011, pp. 1121-1140.

Stella et al., "Aqueous Solubility and Dissolution Rate Does Not Adequately Predict in Vivo Performance: A Probe Utilizing Some N-Acyloxymethyl Phenytoin Prodrugs", Journal of Pharmaceutical Sciences, vol. 88, No. 8, 1999, pp. 775-779.

Sternberg et al., "Progress in the Treatment of Advanced Prostate Cancer," American Society of Clinical Oncology Educational Book, 2014, pp. 117-131.

Tanno et al., "Evaluation of Hypromellose Acetate Succinate (HPMCAS) as a Carrier in Solid Dispersions", Drug Development and Industrial Pharmacy, 2004, vol. 30, No. 1, pp. 9-17.

Tanno, "Evaluation of Characteristics of Hypromellose Acetate Succinate (HPMCAS) as a Carrier for Solid Dispersion: from Study to Improve In Vitro Dissolution of Poorly Water Soluble Drugs", Journal of Pharmaceutical Science and Technology, Japan, vol. 73, No. 4, 2013, pp. 214-222.

Thakral et al. "Eudragit: a technology evaluation" 2012, 1 page.

Vasconcelos et al., "Solid Dispersions as Strategy to Improve Oral Bioavailability of Poor Water Soluble Drugs", Drug Discovery Today, vol. 12, No. 23/24, Dec. 2007, pp. 1068-1075.

Weuts et al., "Physicochemical Properties of the Amorphous Drug, Cast Films, and Spray Dried Powders to Predict Formulation Probability of Success for Solid Dispersions: Etravirine", J. Pharm. Sci., vol. 100, No. 1, Jan. 2011, pp. 264-274.

(56) References Cited

OTHER PUBLICATIONS

Williams et al., "Strategies to Address Low Drug Solubility in Discovery and Development", Pharmacol. Rev., vol. 65, Jan. 2013, pp. 315-499.
Wilson et al., "Relationship Between Amorphous Solid Dispersion In Vivo Absorption and In Vitro Dissolution: Phase Behavior During Dissolution, Speciation, and Membrane Mass Transport", Journal of Controlled Release, vol. 292, 2018, pp. 172-182.
Xun Zhe et al., "Progress in Research and Application of Hydroxypropylmethylcellulose Acetate Succinate", Dec. 31, 2006, pp. 299-307.
Zelboraf, "European Medicines Agency Committee for Medicinal Products for Human Use (CHAMP)", Assessment Report, Dec. 2011, pp. 1-13.
Zhang et al., "Chapter 9, Solid Dispersion Techniques", Peking University Medical Press, 2005, pp. 373-377.
Zhang et al., "Pharmacy of Traditional Chinese Medicine", China Pharmaceutical Science and Technology Press, Feb. 2013, pp. 384-386.
"Bioavailability Study of 3 Tablet Formulations vs. Capsule Formulation of JNJ-56021927 in Fasting Healthy Male Participants," History of Changes for Study: NCT02160756, Nov. 13, 2014 (v6), pp. 1-5.
"European Medicines Agency Committee for Medicinal Products for Human Use", Assessment report, 2011, pp. 1-104.
"European Medicines Agency Evaluation of Medicines for Human Use", CHMP Assessment Report For Intelence (Registered) 2008, pp. 1-52.
"EUDRAGIT® Functional Polymers For Oral Solid Dosage Forms", Retrieved from: http://healthcare.evonik.com/product/health-care/en/products/pharmaceutical-excipients/EUDRAGIT/, Jan. 24, 2018, pp. 1-4.
A Study of JNJ-56021927 (ARN-509) and Abiraterone Acetate in Participants With Metastatic Castration-Resistant Prostate Cancer, History of Changes for Study: NCT02123758, Dec. 2, 2014, (v10), pp. 1-12.
Abbott Receives U.S. FDA Approval for Heat-Stable Norvir(R) (ritonavir) Tablets, Press Release, Feb. 11, 2010, pp. 1-10.
Abbott's new Kaletra tablets approved by EC, Pharmaceutical Industry, 2005, 1 page.
Al-Obaidi et al., "Evaluation of Griseofulvin Binary and Ternary Solid Dispersions with HPMCAS", AAPS Pharm. Sci. Tech., vol. 10, No. 4, Dec. 2009, pp. 1172-1177.
Allawadi et al., "Solid Dispersions: A Review on Drug Delivery System and Solubility Enhancement", IJPSR, 2013, vol. 4, No. 6, pp. 2094-2105.
Aulton, "Pharmaceutics, The Science of Dosage Form Design", 2nd Edition, Table of Contents, 2002, pp. 113-138.
Bajaj et al. "Bioavailability Enhancement: A review", Int. J. Pharma Bio Sci., Apr.-Jun. 2011, pp. 202-216, vol. 2 Issue 2, pp. 202-216.
Beak, "Improved Supersaturation and Oral Absorption of Dutasteride By Amorphous Solid Dispersions", Chem Pharm Bull (Tokyo), Nov. 2012, vol. 60, No. 11, pp. 1468-1473.
Clegg et al., "ARN-509: A Novel Antiandrogen for Prostate Cancer Treatment", Cancer Res; vol. 72, No. 6, Mar. 15, 2012, pp. 1494-1503.
Curatolo et al., "Utility of Hydroxypropylmethykellulose Acetate Succinate (HPMCAS) for Initiation and Maintenance of Drug Supersaturation in the GI Milieu", Pharmaceutical Research, vol. 26, No. 6, Jun. 2009, pp. 1419-1431.
Datasheet for the decision of Feb. 8, 2021, Case No. T 1193 / 18, pp. 1-24.
Declaration by Geert Verreck, Ph.D executed on Mar. 14, 2022, 1 page.
Everolimus, European Medicines Agency, Assessment Report, Jun. 23, 2011, pp. 1-104.
Evidence Reference https://cdn.sanity.io/files/0w8moc6/pharmtech/99d80e288f7f544da430fd67e232879c3213c4b9.pdf, 2014, pp. 1-118.
Examiner communication in relation to equivalent BR 112017011788, published on Mar. 21, 2023.
Examiner communication in relation to equivalent CA 2969656 A, published on Nov. 30, 2022.
Exhibit 36, Opposition, Solid dispersion screen for apalutamide, filed on Mar. 18, 2022 in EP Application No. EP15817642.0.
Exhibit D26, Oppostion, Experimental report of solid dispersions of apalutamide prepared by hot melt extrusion, filed on Mar. 18, 2022 in EP Application No. EP15817642.0.
Exhibit D34, Opposition, Comparative physicochemical data for apalutamide and enzalutamide, filed on Mar. 18, 2022 in EP Application No. EP15817642.0.
Final rejection in relation to equivalent US 2017/360754 Al, published on Oct. 13, 2021.
Friesen et al., "Hydroxypropyl Methylcellulose Acetate Succinate-Based Spray-Dried Dispersions; an Overview", Mol. Pharm., Dec. 1, 2008, vol. 5, No. 6, pp. 1003-1019.
Gupta et al., "Changing Paradigms in Management of Metastatic Castration Resistant Prostate Cancer (mCRPC)," BMC Urology, vol. 14, No. 1, 55, Jul. 25, 2014, pp. 1-8.
Huang, et al., Fundamental aspects of solid dispersion technology for poorly soluble drugs. Acta Pharm Sin B, Dec. 5, 2013, vol. 4, No. 1, pp. 18-25.
Incivo, "European Medicines Agency", Assessment report, Jul. 2011, pp. 1-16.
International Search Report and Written Opinion for Application No. PCT/US2015/063667 mailed Dec. 3, 2015.
Jafari, "Preparation, Characterization and Dissolution of Solid Dispersion of Diclofenac Sodium Using Eudragit E-100", Journal of Applied Pharmaceutical Science, Aug. 31, 2013, vol. 3, No. 08, pp. 167-170.
Janssens et al., "Review: Physical Chemistry of Solid Dispersions", Journal of Pharmacy and Pharmacology, vol. 61, Dec. 2009, pp. 1571-1586.
Kalepu et al., "Oral Lipid-Based Drug Delivery Systems—An Overview", Acta Pharmaceutica Sinica B, vol. 3, No. 6, 2013, pp. 361-372.
Kalydeco, "European Medicines Agency", Assessment Report, Jul. 2011 pp. 1-13.
Konno, "Lnhibitory Effect of Polymer on Solid Dispersion Against Crystallization", Netsu Sokutei, 2011, vol. 38, No. 1, pp. 23-28.
Kumar et al., A Study on Solubility Enhancement Methods for Poorly Water Soluble Drugs, American Journal of Pharmacological Sciences, vol. 1, No. 4, 2013, pp. 67-73.
Kumari et al., "Paramount Role of Solid Dispersion in Enhancement of Solubility", Indo Global Journal of Pharmaceutical Sciences, vol. 3, No. 1, 2013, pp. 78-89.
Li "Interactions between drugs and polymers influencing hot melt extrusion" Royal Pharmacetucal Society, Journal of Pharmacy and Phamracology, 66. pp. 148-166. 2013.
Maeseneer et al., "Battling Resistance Mechanisms in Antihormonal Prostate Cancer Treatment: Novel Agents and Combinations", Urologic Oncology, 12-Jan. 2015, vol. 33, Issue 7, pp. 310-321.
Martz, "Escaping Abiraterone," Science-Business Exchange, vol. 6, No. 1049, 2013, pp. 1-3.
Munyendo, "A Review of Progress and Challenges in Soft Gelatin Capsules Formulations For Oral Administration", International Journal of Pharmaceutical Sciences Review and Research, vol. 10, No. 1, 2011, pp. 20-24.
Narkhede et al., "Enhancement of Solubility of Bicalutamide Drug Using Solid Dispersion Technique," Pharma Science Monitor, vol. 3, No. 4, 2012, pp. 2739-2748.
Nikghalb et al., "Solid Dispersion: Methods and Polymers to increase the solubility of poorly soluble drugs", Journal of Applied Pharmaceutical Sciences, Oct. 2012, vol. 2, No. 10, pp. 170-175.
Park et al., "New Kaletra Tablets FDA Approved: Abbott Press Release", HIV, 2005, pp. 1-3.
Patel et al., "Emerging Molecularly Targeted Therapies in Castration Refractory Prostate Cancer", Prostate Cancer, May 2013, vol. 2013, pp. 1-12.
Posadas et al., "Pharmacokinetics (PK) and Safety of ARN-509 With Abiraterone Acetate (AA) and Prednisome (P) in Patients (pts) With Metastatic Castration-Resistant Prostate Cancer(rnCRPC)", Cancer Research, American Association For Cancer Research, US, 2015, vol. 75, Issue 15, pp. 1-3.

(56) References Cited

OTHER PUBLICATIONS

PTAB decision in relation to equivalent US 2017/360754 A1, affirming final rejection, published on Feb. 2, 2023.
Rathkopf et al., "Phase I Study of ARN-509, A Novel Antiandrogen, in the Treatment of Castration-Resistant Prostate Cancer.", J. Clin. Oncol., 2013, vol. 31, No. 28, pp. 1-2.
Rathkopf et al., "Phase I study of ARN-509, a novel antiandrogen, in the treatment of castration-resistant prostate cancer.", J. Clin. Oncol., 2013, vol. 31, No. 28, abstract.
Reich, "Formulation and physical properties of soft capsules", In: Podczeck F. Jones BE (eds) Pharmaceutical capsules, 2nd Edn. Pharmaceutical Press, London, 2004, pp. 201-212.
Sancheti et al., "Development and Characterization of Bicalutamide-Poloxamer F68 Solid Dispersion Systems," Pharmazie, vol. 63, 2008, pp. 571-575.
U.S. Appl. No. 18/192,244, filed Mar. 29, 2023.
U.S. Appl. No. 15/533,188, filed Jun. 5, 2017.

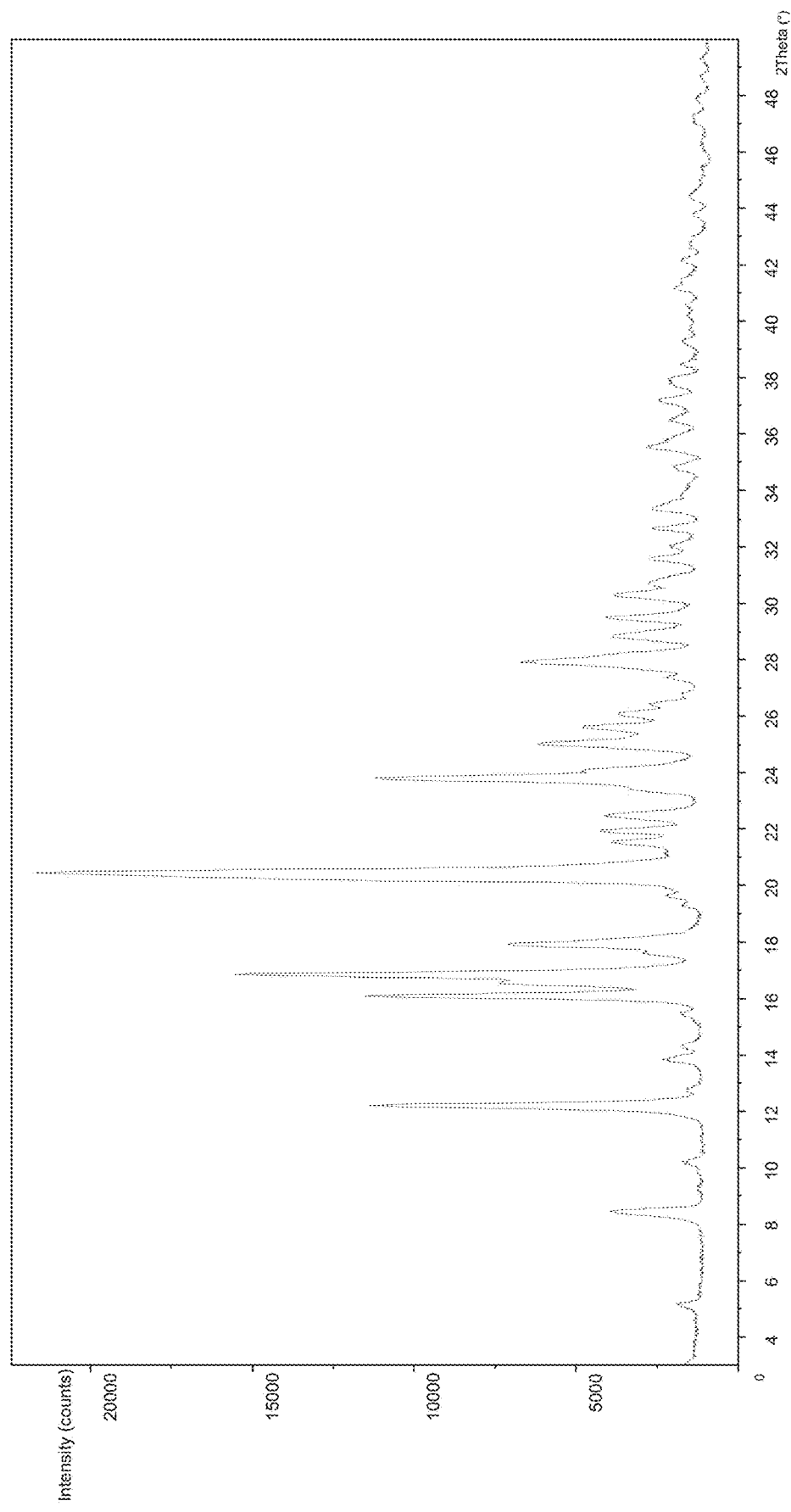
Figure 1: Powder XRD. Diffraction patterns of ARN-509 Form B.

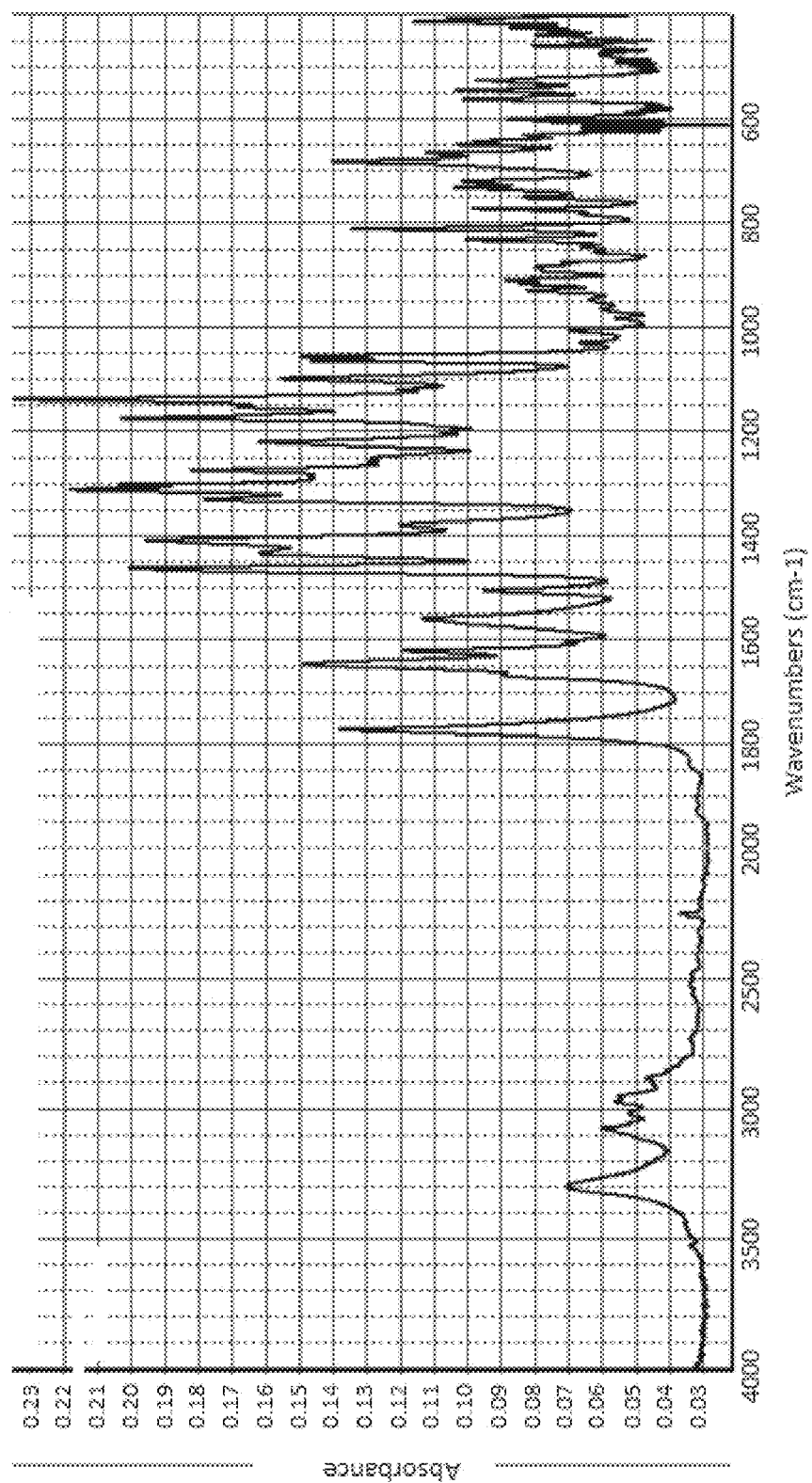
Figure 2: Inared spectrometry (microATR) of ARN-509 Form B.

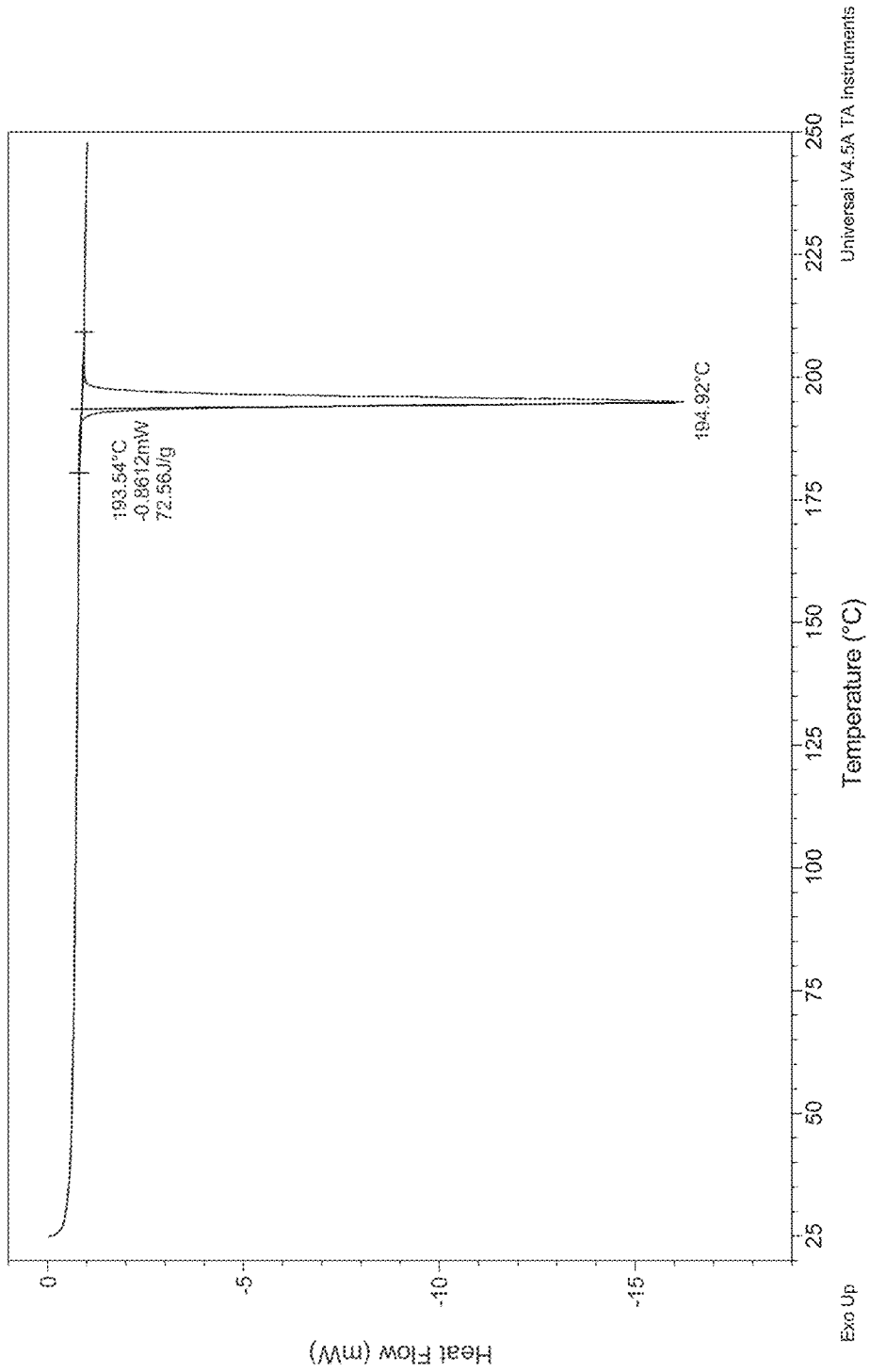
Figure 3: Differential scanning calorimetry (DSC) of ARN-509 Form B.

ANTICANCER COMPOSITIONS

CROSS REFERENCE TO RELATED APPLICATIONS

This application is a continuation of U.S. patent application Ser. No. 18/192,244, filed Mar. 29, 2023, which is a continuation of U.S. patent application Ser. No. 15/533,188, filed Jun. 5, 2017, which is a National Stage Application of International Patent Application No. PCT/US2015/063661, filed 3 Dec. 2015, which claims priority from EP Application 14196594.7, filed 5 Dec. 2014. The complete disclosures of the aforementioned related patent applications are hereby incorporated herein by reference for all purposes.

SUMMARY

The present invention concerns pharmaceutical formulations of ARN-509, which can be administered to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. In one aspect, these formulations comprise a solid dispersion of ARN-509 and HPMCAS. In one aspect, the solid dispersion of ARN-509 and HPMCAS is obtainable, in particular is obtained, by melt-extruding a mixture comprising ARN-509 and HPMCAS and optionally subsequently milling said melt-extruded mixture. In one aspect, the solid dispersion of ARN-509 and HPMCAS is obtainable, in particular is obtained, by spray drying a mixture comprising ARN-509 and HPMCAS in a suitable solvent.

The solid dispersion of ARN-509 and HPMCAS may be further formulated with a pharmaceutically acceptable carrier into a pharmaceutical formulation, such formulation providing improved stability or improved shelf life. With the formulation of the present invention the pill burden for the patient, in particular the cancer patient, can be reduced, and hence therapy adherence and therapy efficiency can be improved.

FIGURES

FIG. 1: XRD pattern of ARN-509 Form B.
FIG. 2: IR spectrum of ARN-509 Form B.
FIG. 3: DSC curve of ARN-509 Form B.

DETAILED DESCRIPTION

ARN-509 is a potent and specific antagonist of the androgen receptor (AR). ARN-509's mechanism of action is antagonism of androgen receptor signaling through inhibition of AR nuclear translocation and DNA binding to androgen response elements.

The actions of androgens with androgen receptors have been implicated in a number of diseases or conditions, such as androgen dependent cancers, virilization in women, and acne, among others. Compounds that diminish the effects of androgens with androgen receptors and/or lower the concentrations of androgen receptors find use in the treatment of diseases or conditions in which androgen receptors play a role.

AR-related diseases or conditions include, but are not limited to, benign prostate hyperplasia, hirsutism, acne, adenomas and neoplasias of the prostate, benign or malignant tumor cells containing the androgen receptor, hyperpilosity, seborrhea, endometriosis, polycystic ovary syndrome, androgenic alopecia, hypogonadism, osteoporosis, suppression of spermatogenesis, libido, cachexia, anorexia, androgen supplementation for age related decreased testosterone levels, prostate cancer, breast cancer, endometrial cancer, uterine cancer, hot flashes, Kennedy's disease muscle atrophy and weakness, skin atrophy, bone loss, anemia, arteriosclerosis, cardiovascular disease, loss of energy, loss of well-being, type 2 diabetes, and abdominal fat accumulation. Given the central role of AR in prostate cancer development and progression, ARN-509 is useful for the treatment of cancer, in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The chemical structure of ARN-509 is:

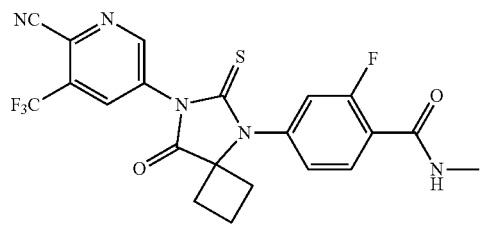 [SMILES: CNC(=O)c1ccc(N2C(=S)N(c3cnc(C#N)c(C(F)(F)F)c3)C(=O)C23CCC3)cc1F]

ARN-509 or 4-[7-(6-cyano-5-trifluoromethylpyridin-3-yl)-8-oxo-6-thioxo-5,7-diazaspiro[3.4]oct-5-yl]-2-fluoro-N-methylbenzamide is currently in clinical development as a nonaqueous, lipid-based solution that is filled into softgel capsules, each containing 30 mg ARN-509. The daily dose being studied is 240 mg/day by oral administration (or 8 softgel capsules). It has been found that in use, the softgel capsules containing ARN-509 have a shelf life of only 6 months and need cold chain storage.

An aspect of the invention relates to pharmaceutical formulations, in particular solid pharmaceutical formulations, more in particular solid pharmaceutical formulations for oral administration of ARN-509, where such formulations have an improved stability, a longer shelf life, or provide for a reduced pill burden for the patient, in particular the cancer patient. The pharmaceutical formulations of the present invention provide a means to increase therapy adherence and therapy efficiency.

An aspect of the invention is a solid dispersion comprising ARN-509 and HPMCAS.

HPMCAS or hydroxypropyl methylcellulose acetate succinate or hypromellose acetate succinate (CAS number 71138-97-1) is a mixture of acetic acid and monosuccinic acid esters of hydroxypropylmethyl cellulose (IUPAC name: cellulose, 2-hydroxypropyl methyl ether, acetate, hydrogen butanedioate). Different grades are available differentiated based on degree/ratio of substitution (acetyl content, succinoyl content) and particle size (micronized and granular). In an aspect of the invention, the HPMCAS in the dispersions with ARN-509 is HPMCAS LG (granular grade) or HPMCAS LF (micronized grade) (Shin-Etsu Chemical Co., Ltd), in particular HPMCAS LG.

An aspect of the invention is a solid dispersion comprising ARN-509 and HPMCAS LG.

An aspect of the invention is a solid dispersion comprising ARN-509 and HPMCAS LF.

An aspect of the invention is a solid dispersion consisting of ARN-509 and HPMCAS.

An aspect of the invention is a solid dispersion consisting of ARN-509 and HPMCAS LG.

An aspect of the invention is a solid dispersion consisting of ARN-509 and HPMCAS LF.

A preferred grade of HPMCAS in the solid dispersions of the invention is HPMCAS LG, because of its better and safer handling properties.

In an aspect of the invention, the weight-by-weight ratio of ARN-509:HPMCAS in the solid dispersion as described herein is in the range from 1:1 to 1:10, preferably from 1:1 to 1:5, more preferably from 1:1 to 1:3 or from 1:2 to 1:3.

In an aspect of the invention, the weight-by-weight ratio of ARN-509:HPMCAS is 1:2. In an aspect of the invention, the weight-by-weight ratio of ARN-509:HPMCAS is 1:3. In an aspect of the invention, the weight-by-weight ratio of ARN-509:HPMCAS LG is 1:2. In an aspect of the invention, the weight-by-weight ratio of ARN-509:HPMCAS LG is 1:3. In an aspect of the invention, the weight-by-weight ratio of ARN-509:HPMCAS LF is 1:2. In an aspect of the invention, the weight-by-weight ratio of ARN-509:HPMCAS LF is 1:3.

An aspect of the invention is a particle consisting of a solid dispersion as described herein.

An aspect of the invention is a particle consisting of a solid dispersion comprising ARN-509 and HPMCAS, in particular wherein the weight-by-weight ratio of ARN-509:HPMCAS is 1:2 or 1:3.

An aspect of the invention is a particle consisting of a solid dispersion comprising ARN-509 and HPMCAS LG, in particular wherein the weight-by-weight ratio of ARN-509:HPMCAS LG is 1:2 or 1:3.

An aspect of the invention is a particle consisting of a solid dispersion comprising ARN-509 and HPMCAS LF, in particular wherein the weight-by-weight ratio of ARN-509:HPMCAS LF is 1:2 or 1:3.

An aspect of the invention is a particle consisting of a solid dispersion consisting of ARN-509 and HPMCAS, in particular wherein the weight-by-weight ratio of ARN-509:HPMCAS is 1:2 or 1:3.

An aspect of the invention is a particle consisting of a solid dispersion consisting of ARN-509 and HPMCAS LG, in particular wherein the weight-by-weight ratio of ARN-509:HPMCAS LG is 1:2 or 1:3.

An aspect of the invention is a particle consisting of a solid dispersion consisting of ARN-509 and HPMCAS LF, in particular wherein the weight-by-weight ratio of ARN-509:HPMCAS LF is 1:2 or 1:3.

An aspect of the invention is a particle comprising a solid dispersion as described hereinabove.

An aspect of the invention is a particle comprising a solid dispersion comprising ARN-509 and HPMCAS, in particular wherein the weight-by-weight ratio of ARN-509:HPMCAS is 1:2 or 1:3.

An aspect of the invention is a particle comprising a solid dispersion comprising ARN-509 and HPMCAS LG, in particular wherein the weight-by-weight ratio of ARN-509:HPMCAS LG is 1:2 or 1:3.

An aspect of the invention is a particle comprising a solid dispersion comprising ARN-509 and HPMCAS LF, in particular wherein the weight-by-weight ratio of ARN-509:HPMCAS LF is 1:2 or 1:3.

An aspect of the invention is a particle comprising a solid dispersion consisting of ARN-509 and HPMCAS, in particular wherein the weight-by-weight ratio of ARN-509:HPMCAS is 1:2 or 1:3.

An aspect of the invention is a particle comprising a solid dispersion consisting of ARN-509 and HPMCAS LG, in particular wherein the weight-by-weight ratio of ARN-509:HPMCAS LG is 1:2 or 1:3.

An aspect of the invention is a particle comprising a solid dispersion consisting of ARN-509 and HPMCAS LF, in particular wherein the weight-by-weight ratio of ARN-509:HPMCAS LF is 1:2 or 1:3.

In an aspect of the invention, the particles as described herein are obtainable, in particular are obtained, by melt-extruding a mixture comprising ARN-509 and HPMCAS and subsequently milling said melt-extruded mixture. In an aspect, the particles as described herein are obtainable, in particular are obtained, by melt-extruding a mixture consisting of ARN-509 and HPMCAS and subsequently milling said melt-extruded mixture. In an aspect, the weight-by-weight ratio of ARN-509 HPMCAS is 1:2 or 1:3.

In an aspect of the invention, the particles as described herein are obtainable, in particular are obtained, by melt-extruding a mixture comprising ARN-509 and HPMCAS LG and subsequently milling said melt-extruded mixture. In an aspect, the particles as described herein are obtainable, in particular are obtained, by melt-extruding a mixture consisting of ARN-509 and HPMCAS LG and subsequently milling said melt-extruded mixture. In an aspect, the weight-by-weight ratio of ARN-509:HPMCAS LG is 1:2 or 1:3.

In an aspect of the invention, the particles as described herein are obtainable, in particular are obtained, by melt-extruding a mixture comprising ARN-509 and HPMCAS LF and subsequently milling said melt-extruded mixture. In an aspect, the particles as described herein are obtainable, in particular are obtained, by melt-extruding a mixture consisting of ARN-509 and HPMCAS LF and subsequently milling said melt-extruded mixture. In an aspect, the weight-by-weight ratio of ARN-509:HPMCAS LF is 1:2 or 1:3.

In an aspect of the invention, the particles as described herein are obtainable, in particular are obtained, by spray drying a mixture comprising ARN-509 and HPMCAS in a suitable solvent. In an aspect, the particles as described herein are obtainable, in particular are obtained, by spray drying a mixture consisting of ARN-509 and HPMCAS in a suitable solvent. In an aspect, the weight-by-weight ratio of ARN-509:HPMCAS is 1:2 or 1:3.

In an aspect of the invention, the particles as described herein are obtainable, in particular are obtained, by spray drying a mixture comprising ARN-509 and HPMCAS LG in a suitable solvent. In an aspect, the particles as described herein are obtainable, in particular are obtained, by spray drying a mixture consisting of ARN-509 and HPMCAS LG in a suitable solvent. In an aspect, the weight-by-weight ratio of ARN-509:HPMCAS LG is 1:2 or 1:3.

In an aspect of the invention, the particles as described herein are obtainable, in particular are obtained, by spray drying a mixture comprising ARN-509 and HPMCAS LF in a suitable solvent. In an aspect, the particles as described herein are obtainable, in particular are obtained, by spray drying a mixture consisting of ARN-509 and HPMCAS LF in a suitable solvent. In an aspect, the weight-by-weight ratio of ARN-509:HPMCAS LF is 1:2 or 1:3.

An aspect of the invention is a pharmaceutical formulation comprising a pharmaceutically acceptable carrier and a solid dispersion as described herein.

An aspect of the invention is a pharmaceutical formulation comprising a pharmaceutically acceptable carrier and particles as described herein.

An aspect of the invention is a pharmaceutical formulation comprising a pharmaceutically acceptable carrier and a solid dispersion, said solid dispersion comprising ARN-509 and HPMCAS. An aspect of the invention is a pharmaceutical formulation comprising a pharmaceutically acceptable carrier and a solid dispersion, said solid dispersion consisting of ARN-509 and HPMCAS. In an aspect, the weight-by-weight ratio of ARN-509:HPMCAS is 1:2 or 1:3.

An aspect of the invention is a pharmaceutical formulation comprising a pharmaceutically acceptable carrier and a solid dispersion, said solid dispersion comprising ARN-509 and HPMCAS LG. An aspect of the invention is a pharmaceutical formulation comprising a pharmaceutically acceptable carrier and a solid dispersion, said solid dispersion consisting of ARN-509 and HPMCAS LG. In an aspect, the weight-by-weight ratio of ARN-509:HPMCAS LG is 1:2 or 1:3.

An aspect of the invention is a pharmaceutical formulation comprising a pharmaceutically acceptable carrier and a solid dispersion, said solid dispersion comprising ARN-509 and HPMCAS LF. An aspect of the invention is a pharmaceutical formulation comprising a pharmaceutically acceptable carrier and a solid dispersion, said solid dispersion consisting of ARN-509 and HPMCAS LF. In an aspect, the weight-by-weight ratio of ARN-509:HPMCAS LF is 1:2 or 1:3.

An aspect of the invention is a pharmaceutical formulation comprising a pharmaceutically acceptable carrier and particles comprising a solid dispersion, said solid dispersion comprising ARN-509 and HPMCAS. An aspect of the invention is a pharmaceutical formulation comprising a pharmaceutically acceptable carrier and particles comprising a solid dispersion, said solid dispersion consisting of ARN-509 and HPMCAS. In an aspect, the weight-by-weight ratio of ARN-509:HPMCAS is 1:2 or 1:3. In an aspect, the particles are obtainable, in particular are obtained, by spray drying as described herein. In an aspect, the particles are obtainable, in particular are obtained, by melt extrusion as described herein.

An aspect of the invention is a pharmaceutical formulation comprising a pharmaceutically acceptable carrier and particles consisting of a solid dispersion, said solid dispersion comprising ARN-509 and HPMCAS. An aspect of the invention is a pharmaceutical formulation comprising a pharmaceutically acceptable carrier and particles consisting of a solid dispersion, said solid dispersion consisting of ARN-509 and HPMCAS. In an aspect, the particles are obtainable, in particular are obtained, by spray drying as described herein. In an aspect, the particles are obtainable, in particular are obtained, by melt extrusion as described herein.

An aspect of the invention is a pharmaceutical formulation comprising a pharmaceutically acceptable carrier and particles comprising a solid dispersion, said solid dispersion comprising ARN-509 and HPMCAS LG. An aspect of the invention is a pharmaceutical formulation comprising a pharmaceutically acceptable carrier and particles comprising a solid dispersion, said solid dispersion consisting of ARN-509 and HPMCAS LG. In an aspect, the weight-by-weight ratio of ARN-509:HPMCAS LG is 1:2 or 1:3. In an aspect, the particles are obtainable, in particular are obtained, by spray drying as described herein. In an aspect, the particles are obtainable, in particular are obtained, by melt extrusion as described herein.

An aspect of the invention is a pharmaceutical formulation comprising a pharmaceutically acceptable carrier and particles comprising a solid dispersion, said solid dispersion comprising ARN-509 and HPMCAS LF. An aspect of the invention is a pharmaceutical formulation comprising a pharmaceutically acceptable carrier and particles comprising a solid dispersion, said solid dispersion consisting of ARN-509 and HPMCAS LF. In an aspect, the weight-by-weight ratio of ARN-509:HPMCAS LF is 1:2 or 1:3. In an aspect, the particles are obtainable, in particular are obtained, by spray drying as described herein. In an aspect, the particles are obtainable, in particular are obtained, by melt extrusion as described herein.

An aspect of the invention is a pharmaceutical formulation comprising a pharmaceutically acceptable carrier and particles consisting of a solid dispersion, said solid dispersion comprising ARN-509 and HPMCAS LG. An aspect of the invention is a pharmaceutical formulation comprising a pharmaceutically acceptable carrier and particles consisting of a solid dispersion, said solid dispersion consisting of ARN-509 and HPMCAS LG. In an aspect, the weight-by-weight ratio of ARN-509:HPMCAS LG is 1:2 or 1:3. In an aspect, the particles are obtainable, in particular are obtained, by spray drying as described herein. In an aspect, the particles are obtainable, in particular are obtained, by melt extrusion as described herein.

An aspect of the invention is a pharmaceutical formulation comprising a pharmaceutically acceptable carrier and particles consisting of a solid dispersion, said solid dispersion comprising ARN-509 and HPMCAS LF. An aspect of the invention is a pharmaceutical formulation comprising a pharmaceutically acceptable carrier and particles consisting of a solid dispersion, said solid dispersion consisting of ARN-509 and HPMCAS LF. In an aspect, the weight-by-weight ratio of ARN-509:HPMCAS LF is 1:2 or 1:3. In an aspect, the particles are obtainable, in particular are obtained, by spray drying as described herein. In an aspect, the particles are obtainable, in particular are obtained, by melt extrusion as described herein.

An aspect of the invention is a solid dispersion as described herein wherein no surfactant is present.

An aspect of the invention is a particle as described herein wherein no surfactant is present.

An aspect of the invention is a pharmaceutical formulation as described herein wherein no surfactant is present.

An aspect of the invention is a solid dispersion as described herein wherein ARN-509 is the only active pharmaceutical ingredient.

An aspect of the invention is a particle as described herein wherein ARN-509 is the only active pharmaceutical ingredient.

An aspect of the invention is a pharmaceutical formulation as described herein wherein ARN-509 is the only active pharmaceutical ingredient.

In the solid dispersions or particles or pharmaceutical formulations as described herein ARN-509 is present in base form or as a pharmaceutically acceptable addition salt, in particular as a pharmaceutically acceptable acid addition salt. Preferably, ARN-509 is present in base form.

The pharmaceutically acceptable addition salts are meant to comprise the therapeutically active non-toxic salt forms. The acid addition salt forms can be obtained by treating the base form of ARN-509 with an appropriate acid, such as inorganic acids, including but not limited to, hydrohalic acids, e.g. hydrochloric acid, hydrobromic acid and the like acids; sulfuric acid; nitric acid; phosphoric acid; metaphosphoric acid and the like acids; or organic acids, including but not limited to, acetic acid, trifluoroacetic acid, trimethylacetic acid, propanoic acid, hydroxyacetic acid, 2-hydroxypropanoic acid, 2-oxopropanoic acid, glycolic acid, oxalic acid, malonic acid, succinic acid, maleic acid, fumaric acid, malic acid, mandelic acid, tartaric acid, 2-hydroxy-1,2,3-propanetricarboxylic acid, methanesulfonic acid, ethanesulfonic acid, 1,2-ethanedisulfonic acid, 2-hydroxyethanesulfonic acid, benzoic acid, cinnamic acid, hydrocinnamic acid, benzenesulfonic acid, 4-methylbenzene-sulfonic acid, 2-naphthalenesulfonic acid, cyclohexanesulfamic acid, 2-hydroxybenzoic acid, 4-amino-2-hydroxybenzoic acid, hexanoic acid, cyclopentanepropionic acid, 3-(4-hydroxybenzoyl)benzoic acid, 4-methylbicyclo-[2.2.2]oct-2-ene-1-carboxylic acid, glucoheptonic acid, tertiary butylacetic acid, lauryl sulfuric acid, gluconic acid, glutamic acid, hydroxynaphthoic acid, stearic acid, muconic acid, butyric acid, phenylacetic acid, phenylbutyric acid, valproic acid, and the like acids.

Conversely said salt forms can be converted by treatment with an appropriate base into the free base form.

Also included are the hydrates, the solvent addition forms and mixtures thereof which ARN-509 and its salts are able to form. Examples of such forms are e.g. hydrates, alcoholates and the like, for instance an ethanolate.

In general, doses employed for adult human treatment are typically in the range from 0.01 mg to 5000 mg per day. In one aspect, doses employed for adult human treatment are from about 1 mg to about 1000 mg per day. In another aspect, doses employed for adult human treatment are from about 100 mg to about 500 mg per day. In another aspect, the dose employed for adult human treatment is 240 mg per day. The exact dosage and frequency of administration of ARN-509 may depend on the particular condition being treated, the severity of the condition being treated, the age, weight and general physical condition of the particular patient as well as other medication the individual may be taking, as is known to those skilled in the art. Furthermore, it is evident that said daily amounts may be lowered or increased depending on the response of the treated subject and/or depending on the evaluation of the physician prescribing ARN-509. The doses mentioned herein are therefore only a guideline and are not intended to limit the scope or use of the invention to any extent. In an aspect of the invention, the daily dose is conveniently presented in a single dose or in divided doses administered simultaneously (or over a short period of time) or at appropriate intervals, for example as two, three, four or more sub-doses per day. In an aspect of the invention, the daily dose is administered in 4 divided doses. In an aspect of the invention, the daily dose is administered in 4 divided doses administered simultaneously (or over a short period of time). In an aspect of the invention, the daily dose is administered in 3 divided doses. In an aspect of the invention, the daily dose is administered in 3 divided doses administered simultaneously (or over a short period of time). In an aspect of the invention, the daily dose is administered in 2 divided doses. In an aspect of the invention, the daily dose is administered in 2 divided doses administered simultaneously (or over a short period of time).

In an aspect of the invention, the pharmaceutical formulation comprises 240 mg of ARN-509.

In an aspect of the invention, the pharmaceutical formulation comprises 120 mg of ARN-509.

In an aspect of the invention, the pharmaceutical formulation comprises 60 mg of ARN-509.

In an aspect of the invention, the pharmaceutical formulation comprises 240 mg of ARN-509. The pharmaceutical formulation is administered once daily.

In an aspect of the invention, the pharmaceutical formulation comprises 120 mg of ARN-509. Two of said formulations are administered daily, preferably simultaneously (or over a short period of time).

In an aspect of the invention, the pharmaceutical formulation comprises 60 mg of ARN-509. Four of said formulations are administered daily, preferably simultaneously (or over a short period of time).

The formulation of the present invention can also be used in combination with another anticancer agent, in particular with another anti prostate cancer agent, more in particular with an androgen biosynthesis inhibitor, that inhibits 17 α-hydroxylase/C17,20-lyase (CYP17), in particular abiraterone acetate. The formulation of the present invention can further be combined with prednisone.

Thus, the present invention also relates to a combination of a pharmaceutical formulation according to the invention and another anticancer agent, in particular another anti prostate cancer agent, more in particular an androgen biosynthesis inhibitor, that inhibits 17 α-hydroxylase/C17,20-lyase (CYP17), in particular abiraterone acetate.

Said combination may further comprise prednisone.

The term "a solid dispersion" means a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion will be called "a solid solution" herein. Solid solutions are preferred physical systems because the components therein are usually readily bioavailable to the organisms to which they are administered. This advantage can probably be explained by the ease with which said solid solutions can form liquid solutions when contacted with a liquid medium such as gastric juice. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions which are less homogenous throughout than solid solutions. Such dispersions are not chemically and physically uniform throughout or comprise more than one phase. For example, the term "a solid dispersion" also relates to a system in a solid state comprising at least two components (a) and (b) and having domains or small regions wherein amorphous, microcrystalline or crystalline (a), or amorphous, microcrystalline or crystalline (b), or both, are dispersed more or less evenly in another phase comprising (b), or (a), or a solid solution comprising (a) and (b). Said domains are regions distinctively marked by some physical feature, small in size compared to the size of the system as a whole, and evenly and randomly distributed throughout the system.

Preferred are solid dispersions or particles as described herein wherein ARN-509 is in a non-crystalline phase as these have an intrinsically faster dissolution rate than those wherein part or all of ARN-509 is in a microcrystalline or crystalline form.

Alternatively, the solid dispersions may be in the form of a dispersion wherein amorphous or microcrystalline ARN-509 or amorphous or microcrystalline HPMCAS is dispersed more or less evenly in a solid solution comprising ARN-509 and HPMCAS.

In an aspect of the invention ARN-509 is present in the solid dispersions as described herein in amorphous form.

In an aspect of the invention the solid dispersion as described herein is a solid solution.

Various techniques exist for preparing the solid dispersions of the invention including melt-extrusion (e.g. hot melt extrusion), spray-drying and solution-evaporation, in particular hot melt-extrusion and spray-drying, spray-drying being preferred.

The particles according to the invention can be prepared by first preparing a solid dispersion of the components, and then optionally grinding or milling said dispersion.

The melt-extrusion process comprises the following steps:
a) mixing ARN-509 and HPMCAS,
b) optionally blending additives with the thus obtained mixture,
c) heating the thus obtained blend until one obtains a homogenous melt,
d) forcing the thus obtained melt through one or more nozzles; and
e) cooling the melt till it solidifies.

The terms "melt" and "melting" do not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

One important parameter of melt extrusion is the temperature at which the melt-extruder is operating. For the melt extrusion process of the present invention, the operating temperature preferably ranges between about 160° C. and about 190° C., more preferably ranges between about 160° C. and 175° C. The lower temperature limit is defined by the point at which ARN-509 is still melting during extrusion with a given set of extrusion conditions. When ARN-509 is not completely molten, the extrudate may not provide the desired bioavailability. When the viscosity of the mixture is too high, the process of melt extrusion will be difficult. At higher temperatures the components may decompose to an unacceptable level. A person skilled in the art will recognize the most appropriate temperature range to be used.

The throughput rate is also of importance because the components may start to decompose when they remain too long in contact with the heating element.

It will be appreciated that the person skilled in the art will be able to optimize the parameters of the melt extrusion process within the above given ranges. The working temperatures will also be determined by the kind of extruder or the kind of configuration within the extruder that is used. Most of the energy needed to melt, mix and dissolve the components in the extruder can be provided by the heating elements. However, the friction of the material within the extruder may also provide a substantial amount of energy to the mixture and aid in the formation of a homogenous melt of the components.

A person skilled in the art will recognize the most appropriate extruder, such as, for example, a single screw, a twin screw extruder or a multi-screw extruder, for the preparation of the subject-matter of the present invention.

Spray-drying of a mixture of the components in a suitable solvent also yields a solid dispersion of said components or particles comprising or consisting of a solid dispersion of said components and may be a useful alternative to the melt-extrusion process, particularly in those cases where the HPMCAS is not sufficiently stable to withstand the extrusion conditions and where residual solvent can effectively be removed from the solid dispersion. Yet another possible preparation consists of preparing a mixture of the components in a suitable solvent, pouring said mixture onto a large surface so as to form a thin film, and evaporating the solvent therefrom.

Solvents suitable for spray-drying can be any organic solvent in which ARN-509 and HPMCAS, in particular HPMCAS LG or HPMCAS LF, are miscable. In an aspect of the invention, the boiling point of the solvent is lower than the Tg (glass transition temperature) of the solid dispersion. In addition, the solvent should have relatively low toxicity and be removed from the dispersion to a level that is acceptable according to The International Committee on Harmonization (ICH) guidelines. Removal of solvent to this level may require a post drying step such as for instance tray-drying, subsequent to the spray-drying process. Solvents include alcohols such as methanol, ethanol, n-propanol, iso-propanol, and butanol, in particular methanol; ketones such as acetone, methyl ethyl ketone and methyl iso-butyl ketone; esters such as ethyl acetate and propylacetate; and various other solvents such as acetonitrile, dichloromethane, toluene, and 1,1,1-trichloroethane. Lower volatility solvents such as dimethyl acetamide or dimethylsulfoxide can also be used. In an aspect of the invention, the solvent suitable for spray drying is a mixture of solvents. In an aspect of the invention the solvent for spray drying is a mixture of an alcohol and dichloromethane, in particular a mixture of methanol and dichloromethane, more in particular a mixture of methanol and dichloromethane 6:4 (w:w) or 5:5 (w/w), 6:4 (w:w) being preferred.

The particles as described herein have a $d^{50}$ of about 1500 μm, of about 1000 μm, of about 500 μm, of about 400 μm, of about 250 μm, of about 200 μm, of about 150 μm, of about 125 μm, of about 100 μm, of about 70 μm, of about 65 μm, of about 60 μm, of about 55 μm, of about 50 μm, of about 45 μm, of about 40 μm, of about 35 μm, of about 30 μm, of about 25 μm, or of about 20 μm. Particles obtained by spray drying have preferably a $d^{50}$-value falling in the range from about 20 μm to about 100 μm, in particular a $d^{50}$-value falling in the range from about 20 μm to about 70 μm, more in particular a $d^{50}$-value of about 20 μm, of about 25 μm, of about 30 μm, of about 35 μm, of about 40 μm, of about 45 μm, of about 50 μm, of about 55 μm, of about 60 μm, of about 65 μm, or of about 70 μm.

As used herein, the term $d^{50}$ has its conventional meaning as known to the person skilled in the art and can be measured by art-known particle size measuring techniques such as, for example, sedimentation field flow fractionation, photon correlation spectroscopy, laser diffraction or disk centrifugation. The $d^{50}$ mentioned herein may be related to volume distributions of the particles. In that instance, by "a $d^{50}$ of 50 μm" it is meant that at least 50% of the volume of the particles has a particle size of less than 50 μm. The same applies to the other particle sizes mentioned. In a similar manner, the $d^{50}$ particle size may be related to weight distributions of the particles. In that instance, by "$d^{50}$ of 50 μm" it is meant that at least 50% of the weight of the particles has a particle size of less than 50 μm. The same applies to the other particle sizes mentioned. Usually volume and weight distribution result in the same or about the same value for the average particle size.

The particle size can be an important factor determining the tabletting speed, in particular the flowability and therefore the manufacturability on a large scale of a particular dosage form or formulation, and the quality of the final product. For instance, for capsules, the particle size may range preferably from about 100 to about 1500 µm ($d^{50}$); for tablets the particle size is preferably less than 250 µm, more preferably less than 100 µm ($d^{50}$). Too small particles (<10-20 µm) often cause sticking on the tablet punches and manufacturability issues.

The particles or solid dispersions as described herein may further comprise one or more pharmaceutically acceptable excipients such as, for example, plasticizers, flavors, colorants, preservatives and the like. Especially in case of preparation by hot melt extrusion, said excipients should not be heat-sensitive, in other words, they should not show any appreciable degradation or decomposition at the working temperature of the melt-extruder.

Suitable plasticizers are pharmaceutically acceptable and include low molecular weight polyalcohols such as ethylene glycol, propylene glycol, 1,2 butylene glycol, 2,3-butylene glycol, styrene glycol; polyethylene glycols such as diethylene glycol, triethylene glycol, tetraethylene glycol; other polyethylene glycols having a molecular weight lower than 1,000 g/mol; polypropylene glycols having a molecular weight lower than 200 g/mol; glycol ethers such as monopropylene glycol monoisopropyl ether; propylene glycol monoethyl ether; diethylene glycol monoethyl ether; ester type plasticizers such as triethyl citrate, sorbitol lactate, ethyl lactate, butyl lactate, ethyl glycolate, allyl glycollate; and amines such as monoethanolamine, diethanolamine, triethanolamine, monoisopropanolamine; triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

In an aspect of the invention, the particles or solid dispersions as described herein do not contain a plasticizer.

The solid dispersions or the particles of the present invention can be formulated into pharmaceutical formulations comprising a therapeutically effective amount of ARN-509. Although, at first instance, pharmaceutical formulations for oral administration such as tablets and capsules are envisaged, the solid dispersions or the particles of the present invention can also be used to prepare pharmaceutical formulations e.g. for rectal administration. Preferred formulations are those adapted for oral administration shaped as a tablet. They can be produced by conventional tabletting techniques with conventional ingredients or excipients (pharmaceutically acceptable carrier) and with conventional tabletting machines. In order to facilitate the swallowing of such a formulation by a mammal, it is advantageous to give the formulations, in particular tablets, an appropriate shape. A film coat on the tablet may further contribute to the ease with which it can be swallowed.

The formulations of the invention, in particular the tablets, may include one or more conventional excipients (pharmaceutically acceptable carrier) such as disintegrants, diluents, fillers, binders, buffering agents, lubricants, glidants, thickening agents, sweetening agents, flavors, and colors. Some excipients can serve multiple purposes. Preferably, the formulations of the present invention include a disintegrant, a diluent or filler, a lubricant and glidant.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 3 to about 15% (w/w) and preferably range from about 3 to 7%, in particular is about 5% (w/w). Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™) Preferred is microcrystalline cellulose and silicified microcrystalline cellulose. The amount of diluent or filler in the tablets may conveniently range from about 20% to about 70% (w/w) and preferably ranges from about 55% to about 60% (w/w).

Lubricants and glidants can be employed in the manufacture of certain dosage forms, and will usually be employed when producing tablets. Examples of lubricants and glidants are hydrogenated vegetable oils, e.g. hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal silica. A preferred lubricant is magnesium stearate. A preferred glidant is colloidal anhydrous silica.

Glidants generally comprise 0.2 to 7.0% of the total tablet weight, in particular 0.5 to 1.5%, more in particular 1 to 1.5% (w/w).

Lubricants generally comprise 0.2 to 7.0% of the total tablet weight, in particular 0.2 to 1%, more in particular 0.5 to 1% (w/w).

Other excipients such as coloring agents and pigments may also be added to the formulations of the invention. Coloring agents and pigments include titanium dioxide and dyes suitable for food. A coloring agent is an optional ingredient in the formulation of the invention, but when used the coloring agent can be present in an amount up to 3.5% based on the total tablet weight.

Flavors are optional in the formulation and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, *eucalyptus*, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, The amount of flavor may depend on a number of factors including the organoleptic effect desired. Generally the flavor will be present in an amount from about 0% to about 3% (w/w).

As known in the art, tablet blends may be dry-granulated or wet-granulated before tabletting. The tabletting process itself is otherwise standard and readily practised by forming a tablet from desired blend or mixture of ingredients into the appropriate shape using a conventional tablet press.

Tablets of the present invention may further be film-coated e.g. to improve taste, to provide ease of swallowing and an elegant appearance. Many suitable polymeric film-coating materials are known in the art. A preferred film-coating material is Opadry II 85F210036 Green. Other suitable film-forming polymers also may be used herein, including, hydroxypropylcellulose, hydroxypropyl methylcellulose (HPMC), especially HPMC 2910 5 mPa·s, and acrylate-methacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In tablets according to the invention, the film coat in terms of weight preferably accounts for about 3% (w/w) or less of the total tablet weight.

Preferred formulations are those wherein the weight of the particles or solid dispersions as described herein ranges from 20 to 40%, in particular from 30 to 40% of the total weight of the formulation.

The present invention further concerns a process of preparing solid dispersions as described herein, comprising blending ARN-509 and HPMCAS and extruding said blend at a temperature in the range from about 160° C. to about 190° C.

The present invention further concerns a process of preparing particles as described herein, comprising blending ARN-509 and HPMCAS, extruding said blend at a temperature in the range from about 160° C. to about 190° C., grinding the extrudate, and optionally sieving the particles.

Suitable extruders that may be used are the Haake miniextruder, Leistritz 18 mm extruder, and the Leistritz 27 mm extruder.

The present invention further concerns a process of preparing particles or solid dispersions as described herein comprising mixing ARN-509 and HPMCAS in a suitable solvent and spray drying said mixture. In an aspect, the suitable solvent is a mixture of dichloromethane and methanol. In an aspect, the suitable solvent is a mixture of dichloromethane and methanol wherein the weight:weight ratio of dichloromethane to methanol in the mixture is 4:6 or 5:5, 4:6 being preferred.

A preferred crystalline form of ARN-509 for preparing the solid dispersions or particles as described herein is Form B, which is an anhydrous crystalline form (see hereinafter and reference is also made to WO2013/184681, which is incorporated herein by reference).

It is another object of the invention to provide a process of preparing a pharmaceutical formulation as described herein, in particular in the form of a tablet or a capsule, characterized by blending a therapeutically effective amount of a solid dispersion or particles as described herein, with a pharmaceutically acceptable carrier and compressing said blend into tablets or filling said blend in capsules.

Further, this invention concerns a solid dispersion or particles as described herein, for use in preparing a pharmaceutical formulation for administration, in particular oral administration, to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The present invention also concerns the use of a solid dispersion or particles as described herein, for the preparation of a pharmaceutical formulation for administration, in particular oral administration, to a mammal, in particular a human, suffering from an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The invention also relates to a method of treating an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer, in a mammal, in particular a human, which comprises administering, in particular orally, to said mammal, in particular human, an effective anticancer amount of a pharmaceutical formulation as described herein.

The invention further concerns the use of a pharmaceutical formulation as specified herein, for the manufacture of a medicament for treating an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer. Or, alternatively, the invention concerns a pharmaceutical formulation as specified herein for use in the treatment of an androgen receptor (AR)-related disease or condition, in particular cancer, more in particular prostate cancer, including but not limited to castration-resistant prostate cancer, metastatic castration resistant prostate cancer, chemotherapy-naive metastatic castration resistant prostate cancer, biochemically relapsed hormone sensitive prostate cancer, or high-risk, non-metastatic castration-resistant prostate cancer.

The invention also relates to a pharmaceutical package suitable for commercial sale comprising a container, a pharmaceutical formulation as described herein, and associated with said package written matter.

The term "about" as used herein in connection with a numerical value is meant to have its usual meaning in the context of the numerical value. Where necessary the word "about" may be replaced by the numerical value ±10%, or ±5%, or ±2%, or ±1%.

All documents cited herein are incorporated by reference in their entirety.

The following examples are intended to illustrate the present invention.

Example 1: ARN-509 Forms

For the preparation of different (crystalline) forms of ARN-509, reference is made to WO2013/184681, which is incorporated herein by reference. Different (crystalline or amorphous) forms of ARN-509 can be used to prepare the solid dispersions, particles or formulations according to the present invention.

A preferred form of ARN-509 for use in the preparation of the solid dispersions, particles or formulations according to the present invention is ARN-509 Form B, which is an anhydrous crystal. It was prepared by suspending ARN-509 Form A (reference is made to WO2013/184681, including for the diffraction data) in USP water and heating the slurry to 55±5° C., holding at said temperature for at least 24 hours, followed by cooling the slurry to 25±5° C. The resulting slurry was filtered, and the wet cake washed once with USP water. The wet cake was unloaded from the filter and dried under vacuum to afford ARN-509 Form B. Reference is also made to Example 2 below.

Solubility of Form A: 0.01 mg/ml in water.
Solubility of Form B: 0.004 mg/ml in water.

Example 2

Characterisation of ARN-509 Form B
Powder XRD

X-ray powder diffraction (XRPD) analyses were carried out on a PANalytical (Philips) X'PertPRO MPD diffractometer. The instrument is equipped with a Cu LFF X-ray tube. The compound was spread on a zero background sample holder.

Instrument Parameters

| generator voltage: | 45 kV |
|---|---|
| generator amperage: | 40 mA |
| geometry: | Bragg-Brentano |
| stage: | spinner stage |

Measurement Conditions

| scan mode: | continuous |
|---|---|
| scan range: | 3 to 50° 2θ |
| step size: | 0.02°/step |
| counting time: | 30 sec/step |
| spinner revolution time: | 1 sec |
| radiation type: | CuKα |

| Incident beam path | | Diffracted beam path | |
|---|---|---|---|
| program, divergence slit: | 15 mm | long anti scatter shield: | + |
| Soller slit: | 0.04 rad | Soller slit: | 0.04 rad |
| beam mask: | 15 mm | Ni filter: | + |
| anti scatter slit: | 1° | detector: | X'Celerator |
| beam knife: | + | | |

The X-ray powder diffraction pattern of ARN-509 Form B shows diffraction peaks without the presence of a halo, indicating that this compound is present as a crystalline product. The XRD pattern of ARN-509 Form B is shown in FIG. 1.

Infrared Spectrometry (Micro ATR-IR)

The samples were analyzed using a suitable microATR accessory.

| apparatus: | Thermo Nexus 670 FTIR spectrometer |
|---|---|
| number of scans: | 32 |
| resolution: | 1 cm$^{-1}$ |
| wavelength range: | 4000 to 400 cm$^{-1}$ |
| detector: | DTGS with KBr windows |
| beamsplitter: | Ge on KBr |
| micro ATR accessory: | Harrick Split Pea with Si crystal |

The spectrum of ARN-509 Form B is shown in FIG. 2.

Differential Scanning Calorimetry (DSC)

The compound was transferred into a standard aluminum TA-Instrument sample pan. The sample pan was closed with the appropriate cover and the DSC curve was recorded on a TA-Instruments Q1000 MTDSC equipped with a RCS cooling unit, using the following parameters:

| initial temperature: | 25° C. |
|---|---|
| heating rate: | 10° C./min |
| final temperature: | 250° C. |

The DSC curve of ARN-509 Form B shows the melting of the product at 194.9° C. with a heat of fusion of 73 J/g. See FIG. 3.

Example 3.1: Preparation of a Solid Dispersion of ARN-509:HPMCAS LG 1:3

| ARN-509 | 2,500 g |
|---|---|
| HPMC-AS LG | 7,500 g |
| Dichloromethane,$^a$ | 76,000 g |
| Methanol $^a$ | 114,000 g |

$^a$ Removed during processing

The dichloromethane and methanol were transferred into a suitable container and stirring was started. Under continuous stirring ARN-509 Form B was added to the solvent mixture and stirred until dissolved. HPMCAS was added to the solution and stirred overnight. A yellowish viscous turbid mixture was obtained. The mixture was filtered inline through a GRID filter. The mixture was spray dried using a suitable spray dryer, e.g. Niro A/S PSD3 with a high pressure nozzle with the following parameters: feed flow of 75 kg/hour, outlet temperature of 46° C. and a condenser temperature of −9° C.

The spray dried product (SDP) was dried in a suitable dryer, e.g. tray dryer using vacuum, nitrogen flow and a drying temperature of 40° C.

Example 3.2: Preparation of Tablets Comprising a Solid Dispersion of ARN-509:HPMCAS 1:3

| Spray dried powder (SDP) of Example 3.1 | 7,200 g |
|---|---|
| Colloidal Anhydrous Silica | 273 g |
| Croscarmellose sodium | 1,050 g |
| Microcrystalline Cellulose | 8,865 g |
| Silicified Microcrystalline Cellulose | 3,507 g |
| Magnesium stearate $^a$ | 105 g |

$^a$ Vegetable grade for 30,000 tablets

The SDP was sieved and mixed with part (10/13) of the colloidal anhydrous silica to a homogeneous blend using a suitable blender. Part (1/2) of the croscarmellose sodium and the microcrystalline cellulose (all) were sieved and added to the blend and mixed using a suitable blender. A dry granulate was made by using a suitable compaction technique, e.g. roller compaction. The silicified microcrystalline cellulose, remainder of the croscarmellose sodium (1/2) and colloidal anhydrous silica (3/13) were sieved and added to the dry granulate and mixed using a suitable blender. The magnesium stearate was sieved, added to the blend and mixed using a suitable blender.

The blend was compressed into tablets (containing 60 mg of ARN 509) using a suitable tablet press.

Example 3.3: Preparation of Coated Tablets

| ARN-509 (60 mg) Tablets (see Example 3.2) | 599.9 g |
|---|---|
| Opadry II 85F210036 Green | 17.997 g |
| Purified Water $^a$ | 71.988 g |

$^a$ Removed during processing per batch of 857 tablets

The purified water was transferred into a suitable container. The coating powder was added and mixed with a suitable mixer. The core tablets were film coated with the coating suspension using a suitable coater.

Example 4.1: Preparation of a Solid Dispersion of ARN-509:HPMCAS LF 1:2

| | |
|---|---|
| ARN-509 | 333.33 mg |
| HPMCAS LF | 666.67 mg |
| Acetone [a] | 19000 mg |

[a] Removed during processing (the reported amounts are for 1 g of SDP (spray dried product))

The acetone was transferred into a suitable container, and HPMCAS and ARN-509 Form B were added. After mixing the ingredients using a suitable mixer, the mixture was spray dried using a suitable spray dryer, e.g. Buchi mini spray dryer with the following parameters: spray rate in the range from 6.2-6.7 gram/minute, outlet temperature in the range from 46° C.-49° C. and a condenser temperature in the range from −18° C. to −21° C.

The spray dried product (SDP) was dried in a suitable dryer, e.g. tray dryer using vacuum, nitrogen flow and a drying temperature of 40° C.

Example 4.2: Preparation of Tablets Comprising a Solid Dispersion of ARN-509:HPMCAS 1:2

| | |
|---|---|
| Spray dried powder of 4.1 (SDP) | 360.0 mg |
| Colloidal Anhydrous Silica | 18.2 mg |
| Croscarmellose sodium | 70.0 mg |
| Silicified Microcrystalline Cellulose | 944.8 mg |
| Magnesium stearate | 7.0 mg |
| (amounts for 1 tablet) | |

The SDP, part (7110/9448) of the silicified microcrystalline cellulose, part (10/13) of the colloidal anhydrous silica and part (1/2) of the croscarmellose sodium were sieved and mixed to a homogenous blend using a suitable blender. A dry granulate was made by using a suitable compaction technique. The remainder of the silicified microcrystalline cellulose (2338/9448), colloidal anhydrous silica (3/13) and croscarmellose sodium (1/2) were sieved and added to the dry granulate and further mixed using a suitable blender. Magnesium stearate was sieved and added to the blend and mixed further using a suitable blender. The blend was compressed into tablets using a suitable tablet press.

Example 5.1: Preparation of a Solid Dispersion of ARN-509:HPMCAS LF 1:3 by Hot Melt Extrusion (HME)

| | |
|---|---|
| ARN-509 | 250 mg |
| HPMCAS LF | 750 mg |

(the reported amounts are for 1 g of HME product)

The HPMCAS and ARN-509 Form B were blended in a suitable recipient using a suitable blender. Hot melt extrusion was performed in a Haake extruder, flush mode, maximum temperature 180° C., screw speed 50 rpm. The hot melt extrudate was collected and milled in a suitable mill. The milled hot melt extrudate was sieved using a suitable sieve (250 μm).

Example 5.2: Preparation of Tablets Comprising a Solid Dispersion of ARN-509:HPMCAS LF 1:3 (HME)

| | |
|---|---|
| HME powder of 5.1 | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |
| (amounts for 1 tablet) | |
| HME powder of 5.1 | 480.0 mg |
| Colloidal Anhydrous Silica | 18.2 mg |
| Croscarmellose sodium | 70.0 mg |
| Silicified Microcrystalline Cellulose | 824.8 mg |
| Magnesium stearate | 7.0 mg |
| (amounts for 1 tablet) | |

The silicified microcrystalline cellulose, croscarmellose sodium and colloidal anhydrous silica were sieved and mixed with the hot melt extrudate to a homogenous blend using a suitable blender. Magnesium stearate was sieved and added to the blend and mixed further using a suitable blender. The blend was compressed into tablets using an eccentric tableting press.

Example 6.1: Preparation of a Solid Dispersion of ARN-509:HPMCAS LF 1:3 SDP

| | |
|---|---|
| ARN-509 | 250.0 mg |
| HPMCAS LF | 750.0 mg |
| Acetone [a] | 19000.0 mg |

[a] Removed during processing (the reported amounts are for 1 g of SDP (spray dried product))

The acetone was transferred into a suitable container and HPMCAS LF and ARN-509 Form B were added. After mixing the ingredients using a suitable mixer, the mixture was spray dried using a suitable spray dryer, e.g. Buchi mini spray dryer with the following parameters: spray rate in the range from 5.9-6.6 gram/minute, outlet temperature in the range from 46° C.-49° C. and a condenser temperature in the range from −15° C. to −21° C.

The spray dried product (SDP) was dried in a suitable dryer, e.g. tray dryer using vacuum, nitrogen flow and a drying temperature of 40° C.

Example 6.2: Preparation of Tablets Comprising a Solid Dispersion of ARN-509:HPMCAS 1:3

| | |
|---|---|
| Spray dried powder of 6.1 (SDP) | 240.0 mg |
| Colloidal Anhydrous Silica | 9.1 mg |
| Croscarmellose sodium | 35.0 mg |
| Silicified Microcrystalline Cellulose | 412.4 mg |
| Magnesium stearate | 3.5 mg |
| (amounts for 1 tablet) | |
| Spray dried powder of 6.1 (SDP) | 480.0 mg |
| Colloidal Anhydrous Silica | 18.2 mg |
| Croscarmellose sodium | 70.0 mg |
| Silicified Microcrystalline Cellulose | 824.8 mg |
| Magnesium stearate | 7.0 mg |
| (amounts for 1 tablet) | |

The SDP, part (2955/4124) of the silicified microcrystalline cellulose, part (10/13) of the colloidal anhydrous silica and part (1/2) of the croscarmellose sodium were sieved and mixed to a homogenous blend using a suitable blender. A dry granulate was made by using a suitable compaction technique. The remainder of the silicified microcrystalline cellulose (1169/4124), colloidal anhydrous silica (3/13) and croscarmellose sodium (1/2) were sieved and added to the dry granulate and further mixed using a suitable blender. Magnesium stearate was sieved and added to the blend and mixed further using a suitable blender. The blend was compressed into tablets using an eccentric tabletting press.

Bioavailability Study

Test System
  Species: Marshall beagle dogs
  Supplier: Marshall Farms, Italy/USA
  Gender and age: male (n=12), approximately 1-7 years
  Body weights: 8-13 kg at the start of the experimental phase Diet and Water Supply:
  Continuous access to water
  Dosing: fasted for about 21 hours before dosing till ±2 hours after dosing.
  Afterwards, dogs had free access to food until the late afternoon.

Test Compound and Formulations
  Formulation 1: 60 mg tablet containing ARN-509-HPMC AS-LF ratio 1/3 SDP
  Formulation 2: 60 mg tablet containing ARN-509-HPMC AS-LF ratio 1/3 HME
  Formulation 3: a nonaqueous, lipid-based solution filled into softgel capsules, each containing 30 mg ARN-509

Blood Sampling and Plasma Preparation
  Blood samples (2 ml on EDTA) were taken from a jugular vein. Within 1 hour of sampling, the blood samples were centrifuged and within 2 hours after the start of centrifugation, plasma was stored in the freezer.

Dose Administration

| Day of Dosing | Formulation | Route | Dose (mg/dog) | Tablet (pcs) | Dog Nos. |
|---|---|---|---|---|---|
| Day 0 | Formulation 1 | PO (gavage) | 60 | 1 | n = 4 |
| | Formulation 2 | PO (gavage) | 60 | 1 | n = 4 |
| | Formulation 3 | PO (gavage) | 60 | 2 | n = 4 |

Bioanalysis
  All study samples were analyzed using a qualified LC-MS/MS method. The samples were subjected to a selective sample cleanup, followed by HPLC-MS/MS.
  HPLC separation was done using non-chiral reversed phase liquid chromatography. Subsequent MS/MS analysis was performed using triple quadrupole mass spectrometry in the Multiple Reaction Monitoring (MRM) mode, optimized for the compound. Samples were quantified against calibration curves prepared to cover the concentration range of the study samples. The curves were prepared in the same matrix as the study samples. For each analytical batch, independent quality control samples, prepared in the same matrix as the samples, were analyzed together with the study samples and calibration curve. All analytical batches were accepted based on calibration curve and QC acceptance criteria in line with the current FDA guidelines.

Data Analysis
  Individual plasma concentration-time profiles were subjected to a pharmacokinetic analysis using validated Phoenix software. A non-compartmental analysis using the linear up/log down trapezoidal rule was used for all data.

Results
  The mean $C_{max}$, $T_{max}$, AUC and $F_{rel}$ values of ARN-509 in male beagle dogs after single oral administration of the 3 formulations are presented below:

| Formulation | 1 | 2 | 3 |
|---|---|---|---|
| $C_{max}$ (ng/ml) | 3900 | 2630 | 4110 |
| $T_{max}$ (h) | 0.5-1 | 1-2 | 1-2 |
| $AUC_{last}$ (ng · h/ml)[1] | 183000 | 159000 | 157000 |
| $AUC_{0-inf}$ (ng · h/ml) | 183000 | 151000[2] | 167000 |
| Frel ($AUC_{last}$ ratios) | 117% | 101% | |

[1] $T_{last}$ in majority of animals was 168 h;
[2] n = 3

Formulation 1: HPMC AS-LF ratio 1/3 (SDP)
Formulation 2: HPMC AS-LF ratio 1/3 (HME)
Formulation 3: softgel reference capsule Stability Tests Performed on Powders of Example 3.1 and 5.1

The tests were performed on the powders packed in LDPE/Alu bags.

1. Appearance Testing

A visual examination was performed on the powder of Example 3.1 and Example 5.1 stored under different storage conditions as indicated in table a1 and a2 below.
The results are reported in the table a1 and a2 below.

2. Water Content

The water content was determined by means of a vaporized coulometric Karl Fischer determination in accordance with USP/Ph. Eur.
Powder of Example 3.1 or Example 5.1 was stored as indicated in table a1 or a2 below.
About 50.00 mg (±5.00 mg) of the sample was weighted accurately into a vial and the vial was crimped securely.
The results are reported in table a1 and a2 below.
The following instrumentation, reagents and solutions and parameters were used.

Instrumentation
  Coulometer: 831 KF Coulometer Metrohm
  Oven: 774 Sample Oven Processor Metrohm
  Generator electrode: Electrode with diaphragm Metrohm 6.0344.100
  Indicator electrode: Double Pt-wire electrode Metrohm 6.0341.100

Reagents and Solutions
  Anode solution: Hydranal Coulomat AG Oven (Fluka 34739)
  Cathode solution: Hydranal Coulomat CG (Fluka 34840)
  Water standard: Hydranal Water Standard 1.00 (Fluka 34828)

Oven Parameters
  Carrier gas: $N_2$
  Flow rate: Setpoint 60 mL/min
    Read out value minimum 20 mL/min
  Oven temperature: 120° C.

Coulometer Parameters
  Titration Parameters
  Extr. time: 60 s
  Drift correction: Auto
  Start Conditions
  Pause: 60 s
  Start drift: maximum 12 µg/min
  Time cond. OK: 10 s
  Stop Parameters
  Rel. drift: 5 µg/min Alternative coulometer parameters may be used provided system suitability requirements are met 3. pXRD Testing for the Detection of Crystalline ARN-509

The physical stability of powder of Example 3.1 and Example 5.1 stored under different storage conditions was followed up using powder X-Ray diffraction. The XRD pattern of the powder was compared to the XRD pattern of the corresponding powder measured at time zero (amorphous product).

The powder was brought on to the zero background sample holder. A X-ray measurement of the sample was performed.

The results are reported in table a1 and a2 below.

The following instrumentation and parameters were used.

Instrumentation

Pananalytical X'Pert PRO MPD diffractometer PW3050/60
X-ray tube Cu LFF PW3373/10
Detector: X'Celerator
Sample stage: spinner
Sample holder: zero background sample holder Instrument Settings Spinner revolution time: 1 rps
Generator voltage: 45 kV
Generator current: 40 mA Optical Components in X-Ray Beam Path
Incident Beam Path:
Programmable divergence slit: irradiated length 15 mm
Soller slit: 0.04 rad
Beam mask: 15 mm
Anti-scatter slit: 1°
Beam knife +
Diffracted Beam Path:
Programmable Anti-scatter slit: 1°
Soller slit: 0.04 rad
Filter: Ni Instrument Parameters Geometry: Bragg-Brentano
Radiation: CuKα
Step size: 0.02°
Scan range: from 3° 2θ to 500 2θ
Counting time per step: 60 sec TABLE a1

Test conditions and results for powders of Example 3.1 stored in LDPE/Alu Bags-appearance and water content and crystallinity results

| Parameter | | | | |
|---|---|---|---|---|
| Storage condition | Storage time (months) | Appearance [a] Visual examination | Water content (%) | Crystallinity |
| 30° C./75% RH | Initial | Pass | 0.6 | Amorphous product |
| | 6 | Pass | 1.0 | Amorphous product |
| | 9 | Pass | 1.0 | Amorphous product |
| | 12 | Pass | 1.7 | Amorphous product |

[a] Pass: White to light yellow, fine to granular powder

TABLE a2

Test conditions and results for powders of Example 5.1 stored in LDPE/Alu Bags-appearance and water content and crystallinity results

| Parameter | | | | |
|---|---|---|---|---|
| Storage condition | Storage time (months) | Appearance [a] Visual examination | Water content (%) | Crystallinity |
| 30° C./75% RH | Initial | Pass | 2.3 | Amorphous product |
| | 6 | Pass | 2.0 | Amorphous product |

[a] Pass: White to light yellow-brownish, fine to granular powder

For the appearance, no substantial stability related changes were observed during storage of the drug product intermediate powder at the different storage conditions.

For the water content, no substantial stability related changes were observed during storage of the drug product intermediate powder at the different storage conditions.

For the crystallinity, no substantial stability related changes were observed during storage of the drug product at the different storage conditions.

4. Assay of ARN-509-Chromatographic Purity

The concentration of ARN-509 and its degradation products in powders of Example 3.1 and Example 5.1 stored under different storage conditions were determined by gradient Reversed-Phase UHPLC with UV Detection.

Powders were stored as indicated in table b1 and b2 below.

Approximately 240.00 mg powder was weighted accurately into a 250-mL volumetric flask. Approximately 125 mL acetonitrile was added by graduated cylinder and the whole was shaken mechanically for 30 minutes and diluted to volume with water till approximately 1 cm under the marker. The whole was shaked up manually vigorously. The sample solution was allowed to equilibrate to ambient temperature and was diluted to volume with water. Just before filtering, the volumetric flask was shaked up manually vigorously. The sample solution was filtered through a chemical resistant 0.2 µm filter. The first 3 mL filtrate were discarded into a waste container, not back into the volumetric flask.

The sample solution is stable for 4 days, if stored in refrigerator, protected from light (closed cabinet).

The results are reported in table b1 and b2 below.

The following solutions and instrumentation and parameters were used.

Mobile Phases
Mobile Phase A
10 mM $NH_4Ac$+0.1% TFA/Acetonitrile (90/10, v/v).
Mobile Phase B
Acetonitrile UHPLC Conditions for Identification, Assay and Chromatographic Purity
Column: Acquity BEH C18, 150 mm length×2.1 mm i.d., 1.7 µm particle size
Column Temperature: 45° C.
Auto-Sampler Temperature: 5° C.
Flow Rate: 0.40 mL/min
Detection: UV
Wavelength: 268 nm
Injection Volume: 3 µL
Data Collection Time: 35 minutes
Analysis Run Time: 40 minutes A linear gradient was programmed as demonstrated in the below table.

Linear Gradient Program

| Time (min) | A (% vol) | B (% vol) |
|---|---|---|
| 0 | 100 | 0 |
| 35 | 30 | 70 |
| 36 | 100 | 0 |
| 40 | 100 | 0 |

TABLE b1

Test conditions and results for powders of Example 3.1 stored in LDPE/Alu Bags-assay and degradation products results

| Parameter | | | Degradation products (%) Total degradation products (sum of all degradation products ≥0.05% (totals are calculated on unrounded results) |
|---|---|---|---|
| Storage condition | Storage time (months) | Assay(%) ARN-509 | |
| 30° C./75% RH | Initial | 99.3 | 0.066 |
| | 6 | 98.9 | 0.11 |
| | 9 | 98.0 | 0.07 |
| | 12 | 98.2 | 0.06 |

TABLE b2

Test conditions and results for powders of Example 5.1 stored in LDPE/Alu Bags-assay and degradation products results

| Parameter | | | Degradation products (%) Total degradation products (sum of all degradation products ≥0.05% (totals are calculated on unrounded results) |
|---|---|---|---|
| Storage condition | Storage time (months) | Assay(%) ARN-509 | |
| 30° C./75% RH | Initial | 96.4 | 0.11 |
| | 6 | 96.3 | 0.08 |

No substantial stability related changes were observed during storage of the drug product intermediate powders at the different storage conditions.

5. Water Activity

The water activity was determined with a Novasina $a_w$-meter.

The test was performed on powders of Example 3.1 and Example 5.1.

The results are reported in table c1 and c2 below.

TABLE c1

Test conditions and results for powders of Example 3.1 stored in LDPE/Alu Bags-Water activity results

| Parameter | | |
|---|---|---|
| Storage condition | Storage time (months) | Water activity |
| 30° C./75% RH | Initial | 0.21 |
| | 12 | 0.38 |

TABLE c2

Test conditions and results for powders of Example 5.1 stored in LDPE/Alu Bags-Water activity results

| Parameter | | |
|---|---|---|
| Storage condition | Storage time (months) | Water activity |
| | Initial | 0.44 |

Stability Tests Performed on Tablets of Example 3.3

Tests were performed on tablets stored in HDPE Bottles with Desiccant (silica gel).

1. Appearance Testing

A visual examination was performed on the tablets of Example 3.3 stored under different storage conditions as indicated in table 1 below.

The results are reported in table 1 below.

2. Water Content

The water content was determined by means of a vaporized coulometric Karl Fischer determination in accordance with USP/Ph. Eur.

Tablets of Example 3.3 were stored as indicated in table 1 below.

Tablets were grinded using a Retsch Mixer Mill. Immediately after grinding, about 50.00 mg (±5.00 mg) of the sample was weighted accurately into a vial and the vial was crimped securely.

The results are reported in table 1 below.

The following instrumentation, reagents and solutions and parameters were used.

Instrumentation
  Coulometer: 831 KF Coulometer Metrohm
  Oven: 774 Sample Oven Processor Metrohm
  Generator electrode: Electrode with diaphragm Metrohm 6.0344.100
  Indicator electrode: Double Pt-wire electrode Metrohm 6.0341.100
Reagents and Solutions
  Anode solution: Hydranal Coulomat AG Oven (Fluka 34739)
  Cathode solution: Hydranal Coulomat CG (Fluka 34840)
  Water standard: Hydranal Water Standard 1.00 (Fluka 34828)
Oven Parameters
  Carrier gas: $N_2$
  Flow rate: Setpoint 60 mL/min
    Read out value minimum 20 mL/min
  Oven temperature: 120° C.
Coulometer Parameters
  Titration Parameters
  Extr. time: 60 s
  Drift correction: Auto
  Start Conditions
  Pause: 60 s
  Start drift: maximum 12 µg/min
  Time cond. OK: 10 s
  Stop Parameters
  Rel. drift: 5 µg/min
  Alternative coulometer parameters may be used provided system suitability requirements are met

TABLE 1

Test conditions and results for tablets of Example 3.3 stored in HDPE Bottles with Desiccant (silica gel)-appearance and water content results

| Storage condition | Storage time (months) | Appearance [a] Visual examination | Water content (%) |
|---|---|---|---|
| | Initial | Pass | 3.8 |
| −20° C. | 1 | Pass | 2.4 |
| 5° C. | 3 | Pass | 2.9 |
| | 6 | Pass | 2.2 |
| | 12 | Pass | 3.2 |
| 25° C./60% RH | 6 | Pass | 2.4 |
| | 12 | Pass | 3.7 |
| 30° C./75% RH | 1 | Pass | 2.4 |
| | 3 | Pass | 3.0 |
| | 6 | Pass | 2.5 |
| | 9 | Pass | 3.2 |
| | 12 | Pass | 3.7 |
| 40° C./75% RH | 1 | Pass | 2.5 |
| | 3 | Pass | 3.3 |
| | 6 | Pass | 3.2 |
| 50° C. | 1 | Pass | 2.2 |
| | 3 | Pass | 2.9 |
| Light ICH | | Pass | 2.3 |

[a] Pass: Greenish colored, oblong tablet

Light ICH: integrated near UV energy not less than 200 W·h/m$^2$, overall illumination not less than 1200 klux·h For the appearance, no substantial stability related changes were observed during storage of the drug product at the different storage conditions.

A slight increase in water content was observed.

3. PXRD Testing for the Detection of Crystalline ARN-509

The physical stability of different tablets of Example 3.3 stored under different storage conditions was followed up using powder X-Ray diffraction. The XRD pattern of the tablets was compared to the XRD pattern of the corresponding tablets at time zero (amorphous product).

One tablet was gently grinded to a fine powder using a mortar and pestle. The powder was loaded into the 16 mm sample holder using the back loading technique. A X-ray measurement of the sample was performed.

The results are reported in table 2 below.

The following instrumentation and parameters were used.

Instrumentation
  Philips X'Pert PRO MPD diffractometer PW3050/60
  X-ray tube Cu LFF PW3373/10
  Detector: X'Celerator
  Sample stage: spinner
  Sample holder: cavity diameter 16 mm, cavity depth 2.5 mm Instrument Settings
  Spinner revolution time: 1 rps
  Generator voltage: 45 kV
  Generator current: 40 mA Optical Components in X-Ray Beam Path
Incident Beam Path:
  Programmable divergence slit: irradiated length 10 mm
  Soller slit: 0.04 rad
  Beam mask: 10 mm
  Anti-scatter slit: 1°
  Beam knife +
Diffracted Beam Path:
  Programmable Anti-scatter slit: 1°
  Soller slit: 0.04 rad
  Filter: Ni Instrument Parameters
  Geometry: Bragg-Brentano
  Radiation: CuKα
  Step size: 0.020
  Scan range: from 3°2θ to 50° 2θ
  Counting time per step: 100 sec

TABLE 2

Test conditions and results for tablets of Example 3.3 stored in HDPE Bottles with Desiccant (silica gel)-crystallinity results

| Storage condition | Storage time (months) | Crystallinity |
|---|---|---|
| | Initial | Amorphous drug substance in drug product |
| −20° C. | 1 | Amorphous drug substance in drug product |
| 5° C. | 3 | Amorphous drug substance in drug product |
| | 6 | Amorphous drug substance in drug product |
| | 12 | Amorphous drug substance in drug product |
| 25° C./60% RH | 6 | Amorphous drug substance in drug product |
| | 12 | Amorphous drug substance in drug product |
| 30° C./75% RH | 1 | Amorphous drug substance in drug product |
| | 3 | Amorphous drug substance in drug product |
| | 6 | Amorphous drug substance in drug product |
| | 9 | Not Tested |
| | 12 | Amorphous drug substance in drug product |
| 40° C./75% RH | 1 | Amorphous drug substance in drug product |
| | 3 | Amorphous drug substance in drug product |
| | 6 | Amorphous drug substance in drug product |
| 50° C. | 1 | Amorphous drug substance in drug product |
| | 3 | Amorphous drug substance in drug product |
| Light ICH | | Amorphous drug substance in drug product |

No substantial stability related changes were observed during storage of the drug product at the different storage conditions.

4. Assay of ARN-509-Chromatographic Purity

The concentration of ARN-509 and its degradation products in tablets of Example 3.3 stored under different storage conditions were determined by gradient Reversed-Phase UHPLC with UV Detection.

Tablets were stored as indicated in table 3 below.

Five tablets were weighted accurately. Mean tablet weight was determined. Tablets were grinded to a fine powder. An amount of homogenized powder equivalent to the mean tablet weight was accurately weighted into a 250-mL volumetric flask. Approximately 125 mL acetonitrile was added by graduated cylinder and the whole was shaken mechanically for 30 minutes and diluted to volume with water till approximately 1 cm under the marker. The whole was shaken up manually vigorously. The sample solution was allowed to equilibrate to ambient temperature and was diluted to volume with water. Just before filtering, the volumetric flask was shaken up manually vigorously. The sample solution was filtered through a chemical resistant 0.45 µm filter. The first 3 mL filtrate was discarded into a waste container, not back into the volumetric flask.

The sample solution is stable for 4 days, if stored in refrigerator, protected from light (closed cabinet).

The results are reported in table 3 below.

The following solutions and instrumentation and parameters were used.

Mobile Phases
Mobile Phase A
  10 mM NH$_4$Ac (aqueous ammonium acetate)+0.1% TFA (trifluoroacetic acid)/Acetonitrile (90/10, v/v).

Mobile Phase B
Acetonitrile
UHPLC Conditions for Identification, Assay and Chromatographic Purity
  Column: Acquity BEH C18, 150 mm length×2.1 mm i.d., 1.7 μm particle size
  Column Temperature: 45° C.
  Auto-Sampler Temperature: 5° C.
  Flow Rate: 0.40 mL/min
  Detection: UV
  Wavelength: 268 nm
  Injection Volume: 3 μL
  Data Collection Time: 35 minutes
  Analysis Run Time: 40 minutes A linear gradient was programmed as demonstrated in the below table.

Linear Gradient Program

| Time (min) | A (% vol) | B (% vol) |
|---|---|---|
| 0 | 100 | 0 |
| 35 | 30 | 70 |
| 36 | 100 | 0 |
| 40 | 100 | 0 |

TABLE 3

Test conditions and results for tablets of Example 3.3 stored in HDPE Bottles with Desiccant (silica gel)-assay and degradation products results

| Parameter | | | Degradation products (%) Total degradation products (sum of all degradation products ≥0.05% (totals are calculated on unrounded results) |
|---|---|---|---|
| Storage condition | Storage time (months) | Assay(%) ARN-509 | |
| −20° C. | Initial | 102.3 | 0.11 |
| | 1 | 97.7 | 0.06 |
| 5° C. | 3 | 100.5 | 0.12 |
| | 6 | 99.7 | 0.07 |
| | 12 | 98.6 | 0.07 |
| 25° C./60% RH | 6 | 100.5 | 0.07 |
| | 12 | 101.3 | 0.11 |
| 30° C./75% RH | 1 | 98.8 | 0.11 |
| | 3 | 98.7 | 0.12 |
| | 6 | 100.4 | 0.07 |
| | 9 | 100.1 | 0.11 |
| | 12 | 99.5 | 0.07 |
| 40° C./75% RH | 1 | 96.2 | 0.06 |
| | 3 | 98.5 | 0.12 |
| | 6 | 101.4 | 0.12 |
| 50° C. | 1 | 100.1 | 0.11 |
| | 3 | 100.6 | 0.07 |
| Light ICH | | 97.5 | 0.07 |

Light ICH: integrated near UV energy not less than 200 W·h/m², overall illumination not less than 1200 klux·h No substantial stability related changes were observed during storage of the drug product at the different storage conditions.

5. Dissolution

The dissolution test was performed using Paddle Apparatus (USP type 2, Ph.Eur., JP.) at 75 rpm in 900 mL of 0.5% (w/v) cetyltrimethylammonium bromide (CTAB) in 0.05 M sodium phosphate buffer pH 4.5.

Samples were taken by Distek® sample needles with solid housing and samples were filtered with Whatman®Spartan® 0.45 μm RC (regenerated cellulose) membrane 30 mm diameter filters.

The determination of the quantity of ARN-509 present in the dissolution samples was based upon an isocratic ultra high performance liquid chromatographic (UHPLC) method with UV detection.

The test was performed on tablets of Example 3.3 stored under different storage conditions as indicated in table 4 below.

The following instrumentation, reagents and solutions and parameters were used.

Instrumentation
  Dissolution Instrument: Paddle apparatus (USP type 2, Ph. Eur., JP).
  UHPLC Instrument: Waters Acquity H-Class with UV detector.
  Data Acquisition System: Waters Empower.
  Analytical Balance: Sensitive to 0.01 g.
  Analytical Balance: Sensitive to 0.01 mg.
  pH Meter: Sensitive to 0.01 pH units.
  Thermometer: Sensitive to 0.1° C.

Reagents and Solutions
Reagents
  Cetrimonium bromide, cetyltrimethylammonium bromide, hexadecyltrimethylammonium bromide, (CTAB): Pro Analysis, 99.0% Purity.
  Sodium phosphate monobasic monohydrate ($NaH_2PO_4 \cdot H_2O$): ACS Grade.
  Trifluoroacetic acid: HPLC Grade, 99.0% Purity.
  Acetonitrile: HPLC Grade.

Mobile Phase
  Mobile Phase A: 0.1% (v/v) TFA in water
  Mobile Phase B: Acetonitrile Procedure
Dissolution Parameters
  Apparatus: Paddle Apparatus (USP type 2, Ph.Eur, JP.).
  Vessels: 1-L glass.
  Rotation Speed: 75 rpm.
  Dissolution Medium: 0.5% (w/v) CTAB in 0.05 M Phosphate Buffer pH 4.5.
  Volume of Medium: 900 mL.
  Medium Degassing: Not Required.
  Medium Replacement: Not Required.
  Temperature: 37.0±0.5° C.
  Sinker: Use no sinker.
  Sample Introduction: Transfer 1 tablet into each dissolution vessel.

Analytical Finish—UHPLC Parameters
Conditions
  Column: Acquity UHPLC® CSH C18 1.7-μm particle size, 2.1×50 mm i.d.
  Column Temperature: 60±5° C.
  Sample Temperature: Ambient.
  Flow Rate: 0.6 mL/min.
  Detection: UV at 242 nm.
  Injection Volume: 3 μL.
  Elution Mode: Isocratic.
  Mobile Phase: 50/50 (v:v), 0.1% TFA in water:Acetonitrile.
  Degas using suitable means.
  Run Time (guide): 1.5 minutes.
  Retention Time (guide): Approximately 0.7 minutes for ARN-509
  Wash Solvent: Acetonitrile.
  Needle Wash: Acetonitrile.
  Seal Wash Solvent: 90/10 (v:v), Water:Acetonitrile.
  Purge Solvent: 90/10 (v:v), Water:Acetonitrile.
  Sampling Rate: 20 points/sec with filter constant normal.

TABLE 4

Test conditions and results for tablets of Example 3.3 stored in HDPE Bottles with Desiccant (silica gel)-Dissolution results

| Storage condition | Storage time (months) | Dissolution mean (%) (min-max) | | | | | | |
|---|---|---|---|---|---|---|---|---|
| | | 5 min | 10 min | 15 min | 20 min | 30 min | 45 min | 60 min |
| | Initial | 65 (64-65) | 87 (86-88) | 94 (93-96) | 97 (96-100) | 99 (97-102) | 100 (97-102) | 100 (98-103) |
| −20° C. | 1 | 64 (63-66) | 85 (84-87) | 92 (91-93) | 95 (94-97) | 97 (95-99) | 97 (95-99) | 97 (95-100) |
| 5° C. | 3 | 65 (63-66) | 87 (85-88) | 94 (92-96) | 97 (95-99) | 99 (97-101) | 99 (97-101) | 99 (97-101) |
| | 6 | 63 (61-64) | 84 (83-86) | 92 (91-94) | 95 (93-97) | 96 (94-100) | 97 (95-100) | 97 (95-100) |
| | 12 | 60 (57-62) | 83 (82-84) | 90 (89-93) | 93 (92-96) | 95 (93-98) | 95 (93-99) | 95 (93-99) |
| 25° C./ 60% RH | 6 | 68 (67-70) | 84 (83-86) | 92 (90-93) | 95 (93-96) | 97 (94-99) | 97 (95-99) | 97 (95-99) |
| | 12 | 63 (62-65) | 85 (84-86) | 93 (92-94) | 96 (95-98) | 98 (97-99) | 99 (97-100) | 99 (97-100) |
| 30° C./ 75% RH | 1 | 63 (60-64) | 85 (84-86) | 93 (91-94) | 96 (94-97) | 98 (95-99) | 98 (95-100) | 98 (96-100) |
| | 3 | 65 (64-66) | 86 (85-86) | 94 (93-95) | 97 (96-98) | 99 (97-100) | 99 (98-100) | 99 (98-100) |
| | 6 | 64 (63-67) | 86 (85-87) | 94 (93-94) | 97 (95-98) | 99 (97-100) | 99 (97-101) | 99 (97-101) |
| | 9 | 62 (61-64) | 85 (84-86) | 92 (91-93) | 95 (94-97) | 98 (95-99) | 98 (96-99) | 98 (96-99) |
| | 12 | 65 (62-66) | 86 (85-87) | 93 (92-94) | 96 (93-98) | 97 (95-100) | 98 (95-100) | 98 (95-100) |
| 40° C./ 75% RH | 1 | 63 (62-65) | 86 (84-87) | 93 (91-94) | 96 (93-98) | 99 (94-101) | 99 (94-102) | 99 (95-101) |
| | 3 | 65 (64-67) | 86 (85-87) | 93 (92-96) | 96 (95-99) | 98 (96-101) | 99 (97-102) | 99 (97-101) |
| | 6 | 66 (65-67) | 86 (85-88) | 93 (92-95) | 96 (94-98) | 97 (95-100) | 97 (96-100) | 97 (96-101) |
| 50° C. | 1 | 64 (63-64) | 86 (84-87) | 94 (92-96) | 97 (95-99) | 99 (97-101) | 100 (97-102) | 100 (98-103) |
| | 3 | 65 (64-65) | 86 (85-87) | 94 (93-96) | 97 (95-100) | 99 (97-102) | 100 (97-103) | 100 (97-103) |
| Light ICH | | 64 (63-65) | 85 (85-86) | 93 (92-94) | 96 (95-97) | 98 (97-99) | 98 (96-99) | 98 (97-99) |

Light ICH: integrated near UV energy not less than 200 W·h/m$^2$, overall illumination not less than 1200 klux·h Light ICH: integrated near UV energy not less than 200 W·h/m$^2$, overall illumination not less than 1200 klux·h No substantial stability related changes were observed during storage of the drug product at the different storage conditions.

6. Water Activity

The water activity was determined with a Novasina $a_w$-meter.

The test was performed on tablets of Example 3.3.

The results are reported in table 5 below.

TABLE 5

Test conditions and results for tablets of Example 3.3 stored in HDPE Bottles with Desiccant (silica gel)-Water activity results

| Parameter | | |
|---|---|---|
| Storage condition | Storage time (months) | Water activity |
| | Initial | 0.50 |
| 5° C. | 12 | 0.14 |
| 25° C./60% RH | 12 | 0.22 |
| 30° C./75% RH | 12 | 0.27 |

A slight decrease in water activity was observed after 12 months storage at the tested conditions.

7. Microbiological Purity

The microbiological purity of the tablets of Example 3.3 was tested according to USP <61> and <62>, and Ph.Eur.2.6.12 and 2.6.13.

Results are reported in table 6 below.

TABLE 6

Test conditions and results for tablets of Example 3.3 stored in HDPE Bottles with Desiccant (silica gel)-Microbiological Purity Results

| Parameter Storage condition | Storage time (months) | Total Aerobic Microbial count (cfu/g) USP <61>/ Ph. Eur. 2.6.12 | Total combined Molds and Yeasts Count (cfu/g) USP <61>/ Ph. Eur. 2.6.12 | Pathogens: E. Coli USP <62>/ Ph. Eur. 2.6.13 |
|---|---|---|---|---|
| | Initial | <50 | <50 | Absent in 1 g |
| 5° C. | 12 | <50 | <50 | Absent in 1 g |
| 25° C./ 60% RH | 12 | <50 | <50 | Absent in 1 g |
| 30° C./ 75% RH | 12 | <50 | <50 | Absent in 1 g |

The invention claimed is:

1. A solid dispersion comprising

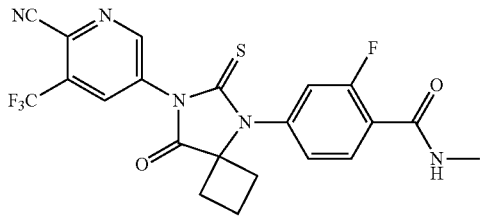 [SMILES: CNC(=O)c1ccc(N2C(=S)N(c3cnc(C#N)c(C(F)(F)F)c3)C(=O)C23CCC3)cc1F]

(ARN-509) and hydroxypropyl methylcellulose acetate succinate (HPMCAS).

2. The solid dispersion according to claim 1 wherein the dispersion consists of ARN-509 and HPMCAS.

3. The solid dispersion according to claim 1 wherein ARN-509 and HPMCAS are present in the solid dispersion in a weight-by-weight ratio of ARN-509: HPMCAS in a range of from 1:1 to 1:5.

4. The solid dispersion according to claim 3 wherein the weight-by-weight ratio of ARN-509: HPMCAS in the solid dispersion is 1:3.

5. The solid dispersion according to claim 3 wherein the weight-by-weight ratio of ARN-509: HPMCAS in the solid dispersion is 1:2.

6. The solid dispersion according to claim 3 wherein the weight-by-weight ratio of ARN-509: HPMCAS in the solid dispersion is 1:1.

7. The solid dispersion according to claim 1 wherein ARN-509 is present in an amorphous form.

8. The solid dispersion according to claim 1 wherein the dispersion is a solid solution.

9. The solid dispersion according to claim 1 wherein the HPMCAS is HPMCAS LG.

10. The solid dispersion according to claim 1 obtainable by spray drying.

11. The solid dispersion according to claim 1 obtainable by hot melt extrusion.

12. The solid dispersion according to claim 1 wherein the HPMCAS is HPMCAS LG or HPMCAS LF and the weight-by-weight ratio of ARN-509: HPMCAS LG or HPMCAS LF in the solid dispersion is 1:2 or 1:3.

13. A particle consisting of the solid dispersion as defined in claim 1.

14. The particle according to claim 13 wherein the HPMCAS is HPMCAS LG or HPMCAS LF and the weight-by-weight ratio of ARN-509: HPMCAS LG or HPMCAS LF in the solid dispersion is 1:2 or 1:3.

15. A particle comprising the solid dispersion as defined in claim 2.

16. A pharmaceutical formulation comprising a pharmaceutically acceptable carrier and the solid dispersion according to claim 1.

17. The pharmaceutical formulation according to claim 16 wherein the HPMCAS is HPMCAS LG or HPMCAS LF and the weight-by-weight ratio of ARN-509: HPMCAS LG or HPMCAS LF in the solid dispersion is 1:2 or 1:3.

18. The pharmaceutical formulation according to claim 16 wherein the formulation comprises 60 mg of ARN-509.

19. The pharmaceutical formulation according to claim 16 wherein the formulation comprises 120 mg of ARN-509.

20. The pharmaceutical formulation according to claim 16 wherein the formulation comprises 240 mg of ARN-509.

21. The pharmaceutical formulation according to claim 16 wherein the solid dispersion is present in a weight range of from 20 to 40% of the total weight of the formulation.

22. The pharmaceutical formulation according to claim 16 wherein the formulation is a tablet.

23. The pharmaceutical formulation according to claim 22 wherein the tablet is suitable for oral administration.

24. A pharmaceutical formulation comprising a pharmaceutically acceptable carrier and a plurality of particles according to claim 13.

25. The pharmaceutical formulation according to claim 24 wherein the HPMCAS is HPMCAS LG or HPMCAS LF and the weight-by-weight ratio of ARN-509: HPMCAS LG or HPMCAS LF in the solid dispersion is 1:2 or 1:3.

26. A pharmaceutical formulation comprising a pharmaceutically acceptable carrier and the solid dispersion according to claim 4.

27. The pharmaceutical formulation according to claim 26 wherein the formulation comprises 60 mg of ARN-509.

28. A process for preparing the solid dispersion according to claim 10 comprising mixing ARN-509 and HPMCAS in a suitable solvent and spray drying said mixture.

29. The process according to claim 28 wherein the suitable solvent is a mixture of dichloromethane and methanol.

30. The process according to claim 29 wherein dichloromethane and methanol are present in the mixture in a weight-by-weight ratio of 4:6.

* * * * *